United States Patent
Hein et al.

(10) Patent No.: US 10,566,138 B2
(45) Date of Patent: *Feb. 18, 2020

(54) HEIN ELECTRO-POLARIZABLE COMPOUND AND CAPACITOR THEREOF

(71) Applicant: Capacitor Sciences Incorporated, Menlo Park, CA (US)

(72) Inventors: Samuel Hein, Fremont, CA (US); Carine Edder, Redwood City, CA (US); Pavel Ivan Lazarev, Menlo Park, CA (US)

(73) Assignee: CAPACITOR SCIENCES INCORPORATED, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/870,504

(22) Filed: Jan. 12, 2018

(65) Prior Publication Data

US 2018/0137978 A1     May 17, 2018

Related U.S. Application Data

(63) Continuation-in-part of application No. 15/163,595, filed on May 24, 2016, now Pat. No. 10,153,087, which is a continuation-in-part of application No. 15/090,509, filed on Apr. 4, 2016, now Pat. No. 9,978,517, application No. 15/870,504, which is a continuation-in-part of application No. 15/818,474, filed on Nov. 20, 2017.

(51) Int. Cl.

| | |
|---|---|
| H01G 4/14 | (2006.01) |
| H01G 4/005 | (2006.01) |
| H01G 4/32 | (2006.01) |
| C07D 471/22 | (2006.01) |
| C07F 7/08 | (2006.01) |
| C09K 19/60 | (2006.01) |
| C09K 19/32 | (2006.01) |
| C09K 19/34 | (2006.01) |
| C09K 19/22 | (2006.01) |
| H01G 4/18 | (2006.01) |
| C09K 19/30 | (2006.01) |

(52) U.S. Cl.
CPC ............. *H01G 4/14* (2013.01); *C07D 471/22* (2013.01); *C07F 7/0812* (2013.01); *C09K 19/22* (2013.01); *C09K 19/322* (2013.01); *C09K 19/3447* (2013.01); *C09K 19/3472* (2013.01); *C09K 19/3477* (2013.01); *C09K 19/606* (2013.01); *H01G 4/005* (2013.01); *H01G 4/32* (2013.01)

(58) Field of Classification Search
None
See application file for complete search history.

(56) References Cited

U.S. PATENT DOCUMENTS

| | | |
|---|---|---|
| 4,549,034 A | 10/1985 | Sato et al. |
| 5,141,837 A | 8/1992 | Nguyen et al. |
| 5,597,661 A | 1/1997 | Takeuchi et al. |

(Continued)

FOREIGN PATENT DOCUMENTS

| | | |
|---|---|---|
| CA | 2074848 A1 | 2/1998 |
| CN | 1582506 A | 2/2005 |

(Continued)

OTHER PUBLICATIONS

Extended European Search Report dated Aug. 8, 2018 for European Patent Application No. 16756391.5.

(Continued)

*Primary Examiner* — Zinna Northington Davis
(74) *Attorney, Agent, or Firm* — BCF LLP.

(57) ABSTRACT

An electro-polarizable compound has the following general formula:

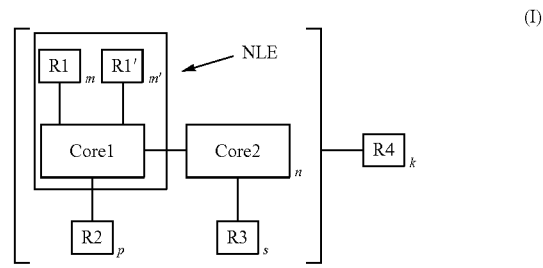

(I)

Core1 is an aromatic polycyclic conjugated molecule having two-dimensional flat form and that self-assembles to form supramolecular structures. R1 are electron donor groups connected to Core1 and R1' are electron acceptor groups connected to Core1, m is number of acceptor groups R1, m' is a number of donor groups R'. The numbers m and m' are equal to 0, 1, 2, 3, 4, 5 or 6, but both m and m' are not both equal to 0. R2 is a substituent comprising one or more ionic groups connected to Core1 directly or via a connecting group; a number p of ionic groups R2 is 0, 1, 2, 3 or 4. The fragment marked NLE has a nonlinear effect of polarization. Core2 is a self-assembling electro-conductive oligomer, a number n of the such oligomers is 0, 2, or 4. R3 is a substituent comprising one or more ionic groups connected to Core2; a number s of the ionic groups R3 is 0, 1, 2, 3 or 4. R4 is a resistive substituent electrically insulating the supramolecular structures from each other. A number k of substituents R4 is 0, 1, 2, 3, 4, 5, 6, 7 or 8.

14 Claims, 2 Drawing Sheets

(56) References Cited

U.S. PATENT DOCUMENTS

| | | | |
|---|---|---|---|
| 6,025,094 | A | 2/2000 | Visco et al. |
| 6,519,136 | B1 | 2/2003 | Chu et al. |
| 7,342,755 | B1 | 3/2008 | Horvat et al. |
| 7,625,497 | B2 | 12/2009 | Iverson et al. |
| 7,795,431 | B2 | 9/2010 | Pschirer et al. |
| 7,910,736 | B2 | 3/2011 | Koenemann et al. |
| 7,990,679 | B2 | 8/2011 | Ehrenberg et al. |
| 8,372,527 | B2 | 2/2013 | Morishita et al. |
| 8,766,566 | B2 | 7/2014 | Baba et al. |
| 8,831,805 | B2 | 9/2014 | Izumi et al. |
| 9,899,150 | B2 | 2/2018 | Lazarev |
| 9,916,931 | B2 | 3/2018 | Lazarev |
| 9,978,517 | B2 | 5/2018 | Lazarev et al. |
| 10,153,087 | B2 * | 12/2018 | Lazarev .................. C09B 5/62 |
| 2003/0103319 | A1 | 6/2003 | Kumar et al. |
| 2003/0105365 | A1 | 6/2003 | Smith et al. |
| 2003/0160595 | A1 | 8/2003 | Provanzana et al. |
| 2004/0223291 | A1 | 11/2004 | Naito et al. |
| 2007/0181973 | A1 | 8/2007 | Hung et al. |
| 2008/0002329 | A1 | 1/2008 | Pohm et al. |
| 2008/0008949 | A1 | 1/2008 | Wu et al. |
| 2008/0266750 | A1 | 10/2008 | Wu et al. |
| 2008/0283283 | A1 | 11/2008 | Abe et al. |
| 2009/0184355 | A1 | 7/2009 | Brederlow et al. |
| 2010/0172066 | A1 | 7/2010 | Baer et al. |
| 2010/0309606 | A1 | 12/2010 | Allers et al. |
| 2011/0042649 | A1 | 2/2011 | Duvall et al. |
| 2011/0079773 | A1 | 4/2011 | Wasielewski et al. |
| 2012/0008251 | A1 | 1/2012 | Yu et al. |
| 2012/0033342 | A1 | 2/2012 | Ito et al. |
| 2012/0059307 | A1 | 3/2012 | Harris et al. |
| 2013/0056720 | A1 | 3/2013 | Kim et al. |
| 2013/0224473 | A1 | 8/2013 | Tassell et al. |
| 2013/0342967 | A1 | 12/2013 | Lai et al. |
| 2014/0035100 | A1 | 2/2014 | Cho |
| 2014/0036410 | A1 | 2/2014 | Okamatsu et al. |
| 2014/0169104 | A1 | 6/2014 | Kan et al. |
| 2014/0316387 | A1 | 10/2014 | Harris et al. |
| 2015/0008671 | A1 | 1/2015 | Rentero et al. |
| 2016/0001662 | A1 | 1/2016 | Miller et al. |
| 2016/0340368 | A1 | 11/2016 | Lazarev |
| 2017/0133167 | A1 | 5/2017 | Keller et al. |
| 2017/0232853 | A1 | 8/2017 | Lazarev et al. |
| 2017/0236641 | A1 | 8/2017 | Furuta et al. |
| 2017/0236642 | A1 | 8/2017 | Furuta et al. |
| 2017/0287637 | A1 | 10/2017 | Lazarev et al. |
| 2017/0301467 | A1 | 10/2017 | Lazarev et al. |
| 2018/0033554 | A1 | 2/2018 | Li et al. |
| 2018/0061582 | A1 | 3/2018 | Furuta et al. |
| 2018/0122143 | A1 | 5/2018 | Ellwood |
| 2018/0126857 | A1 | 5/2018 | Kelly-Morgan |
| 2018/0137978 | A1 | 5/2018 | Hein et al. |
| 2018/0137984 | A1 | 5/2018 | Furuta et al. |
| 2018/0158616 | A1 | 6/2018 | Lazarev et al. |

FOREIGN PATENT DOCUMENTS

| | | |
|---|---|---|
| CN | 100449661 | 1/2009 |
| CN | 1748271 B | 6/2010 |
| CN | 102426918 A | 4/2012 |
| CN | 103755703 A | 4/2014 |
| CN | 103258656 B | 8/2015 |
| EP | 2108673 A1 | 10/2009 |
| EP | 1990682 B1 | 1/2015 |
| JP | 2000100484 A | 4/2000 |
| JP | 2001093778 A | 4/2001 |
| WO | 2009144205 A1 | 12/2009 |
| WO | 2009158553 A2 | 12/2009 |
| WO | 2011137137 A1 | 11/2011 |
| WO | 2012142460 A1 | 10/2012 |
| WO | 2013085467 A1 | 6/2013 |

OTHER PUBLICATIONS

Extended European Search Report dated Sep. 24, 2018 for European Patent Application No. 15856609.1.
Extended European Search Report dated Sep. 26, 2018 for European Patent Application No. 16797411.2.
Final Office Action for U.S. Appl. No. 15/043,247, dated Oct. 24, 2018.
Final Office Action for U.S. Appl. No. 15/043,249, dated Feb. 6, 2018.
Final Office Action for U.S. Appl. No. 15/043,315, dated Jun. 7, 2018.
Final Office Action for U.S. Appl. No. 15/194,224, dated Jan. 30, 2018.
Final Office Action for U.S. Appl. No. 15/449,587, dated Oct. 10, 2018.
Final Office Action for U.S. Appl. No. 15/710,587, dated Nov. 6, 2018.
International Search Report and Written Opinion dated Jul. 31, 2017 for International Patent Application PCT/US2017/024589.
International Search Report and Written Opinion dated Feb. 23, 2018 for International Patent Application No. PCT/US17/64252.
International Search Report and Written Opinion dated Jun. 7, 2017 for International Application No. PCT/US2017/24589, to Pavel Ivan Lazarev, filed Jun. 7, 2017.
M. Jurow et al, "Porphyrins as molectular electronic components of functional devices", Coordination Chemistry Reviews, Elsevier Science, Amsterdam NL, vol. 254, No. 19-20, Oct. 1, 2010, pp. 2297-2310.
Non-Final Action for U.S. Appl. No. 15/043,186, dated Feb. 14, 2018.
Non-Final Office Action for U.S. Appl. No. 15/043,247, dated Jun. 7, 2018.
Non-Final Office Action for U.S. Appl. No. 15/163,595, dated Jan. 17, 2018.
Non-Final Office Action for U.S. Appl. No. 15/430,339, dated Jul. 11, 2018.
Non-Final Office Action for U.S. Appl. No. 15/430,307, dated Jul. 16, 2018.
Non-Final Office Action for U.S. Appl. No. 15/449,587, dated May 21, 2018.
Non-Final Office Action for U.S. Appl. No. 15/710,587, dated Jul. 3, 2018.
Non-Final Office Action for U.S. Appl. No. 15/782,752, dated Sep. 21, 2018.
Non-Final Office Action for U.S. Appl. No. 15/801,240, dated Oct. 19, 2018.
Non-Final Office Action for U.S. Appl. No. 15/805,016, dated Jun. 4, 2018.
Non-Final Office Action for U.S. Appl. No. 15/805,016, dated Sep. 4, 2018.
Non-Final/Final Office Action for U.S. Appl. No. 15/043,247, dated Feb. 20, 2018.
Non-Final/Final Office Action for U.S. Appl. No. 15/430,391, dated Jul. 20, 2018.
Notice of Allowance for U.S. Appl. No. 14/710,480, dated Jan. 11, 2018.
Notice of Allowance for U.S. Appl. No. 14/719,072, dated Nov. 16, 2017.
Notice of Allowance for U.S. Appl. No. 14/919,337, dated Mar. 5, 2018.
Notice of Allowance for U.S. Appl. No. 14/931,757, dated Feb. 8, 2018.
Notice of Allowance for U.S. Appl. No. 15/090,509, dated Jan. 24, 2018.
Notice of Allowance for U.S. Appl. No. 15/163,595, dated Jul. 30, 2018.
Office Action dated May 18, 2018 for Chinese Patent Application for Invention No. 201580025110.
Office Action dated Jan. 25, 2018 for Chinese patent application No. 20158005146.4.
Search Report and Written Opinion dated Feb. 7, 2018 for Singapore Patent Application No. 11201609435W.

(56) References Cited

OTHER PUBLICATIONS

Supplementary Notice of Allowance for U.S. Appl. No. 14/752,600, dated Dec. 4, 2017.
Taiwanese Office Action for 886103 Application No. 106142206, dated Jul. 5, 2018.
Updated Notice of Allowance for U.S. Appl. No. 14/710,480, dated Jan. 17, 2018.
Zhao et al., Theoretical study of one-photon and two-photon absorption properties of perylene tetracarboxylic derivatives, Journal of Chemical Physics, 129(1), 2008.
International Search Report issued in corresponding International application No. PCT/US2018/061874 dated Mar. 21, 2019.

* cited by examiner

HEIN ELECTRO-POLARIZABLE COMPOUND AND CAPACITOR THEREOF

CLAIM OF PRIORITY

This application is a continuation-in-part of U.S. patent application Ser. No. 15/090,509 filed Apr. 4, 2016, U.S. patent application Ser. No. 15/163,595 filed May 24, 2016, and U.S. patent application Ser. No. 15/818,474 filed Nov. 20, 2017, the entire contents of which are incorporated herein by reference.

FIELD OF THE INVENTION

The present disclosure relates generally to passive components of electrical circuit and more particularly to an electro-polarizable compound and capacitor based on this material and intended for energy storage.

BACKGROUND

A capacitor is a passive electronic component that is used to store energy in the form of an electrostatic field, and comprises a pair of electrodes separated by a dielectric layer. When a potential difference exists between the two electrodes, an electric field is present in the dielectric layer. An ideal capacitor is characterized by a single constant value of capacitance, which is a ratio of the electric charge on each electrode to the potential difference between them. For high voltage applications, much larger capacitors are necessary.

One important characteristic of a dielectric material is its breakdown field. The breakdown field corresponds to the value of electric field strength at which the material suffers a catastrophic failure and conducts electricity between the electrodes. For most capacitor geometries, the electric field in the dielectric can be approximated by the voltage between the two electrodes divided by the spacing between the electrodes, which is usually the thickness of the dielectric layer. Since the thickness is usually constant it is more common to refer to a breakdown voltage, rather than a breakdown field. There are a number of factors that can dramatically reduce the breakdown voltage. In particular, the geometry of the conductive electrodes is important factor affecting breakdown voltage for capacitor applications. In particular, sharp edges or points hugely increase the electric field strength locally and can lead to a local breakdown. Once a local breakdown starts at any point, the breakdown will quickly "trace" through the dielectric layer until it reaches the opposite electrode and causes a short circuit.

Breakdown of the dielectric layer usually occurs as follows. Intensity of an electric field becomes high enough to "pull" electrons from atoms of the dielectric material and makes them conduct an electric current from one electrode to another. Presence of impurities in the dielectric or imperfections of the crystal structure can result in an avalanche breakdown as observed in semiconductor devices.

Another important characteristic of a dielectric material is its dielectric permittivity. Different types of dielectric materials are used for capacitors and include ceramics, polymer film, paper, and electrolytic capacitors of different kinds. The most widely used polymer film materials are polypropylene and polyester. Increasing dielectric permittivity allows for increasing volumetric energy density, which makes it an important technical task.

Second-order nonlinear optical (NLO) effects of organic molecules have been extensively investigated for their advantages over inorganic crystals. Properties studied, for example, include their large optical non-linearity, ultra-fast response speed, high damage thresholds and low absorption loss, etc. Particularly, organic thin films with excellent optical properties have tremendous potential in integrated optics such as optical switching, data manipulation and information processing. Among organic NLO molecules, azo-dye chromophores have been a special interest to many investigators because of their relatively large molecular hyper-polarizability (b) due to delocalization of the p-electronic clouds. They were most frequently either incorporated as a guest in the polymeric matrix (guest-host polymers) or grafted into the polymeric matrix (functionalized polymers) over the past decade.

Hyper-electronic polarization of organic compounds is described in greater detail in Roger D. Hartman and Herbert A. Pohl, "Hyper-electronic Polarization in Macromolecular Solids", Journal of Polymer Science: Part A-1 Vol. 6, pp. 1135-1152 (1968). Hyper-electronic polarization may be viewed as the electrical polarization external fields due to the pliant interaction with the charge pairs of excitons, in which the charges are molecularly separated and range over molecularly limited domains. In this article four polyacene quinone radical polymers were investigated. These polymers at 100 Hz had dielectric constants of 1800-2400, decreasing to about 58-100 at 100,000 Hz. Essential drawback of the described method of production of material is use of a high pressure (up to 20 kbars) for forming the samples intended for measurement of dielectric constants.

SUMMARY

The present disclosure provides an electro-polarizable compound having the following general formula (I):

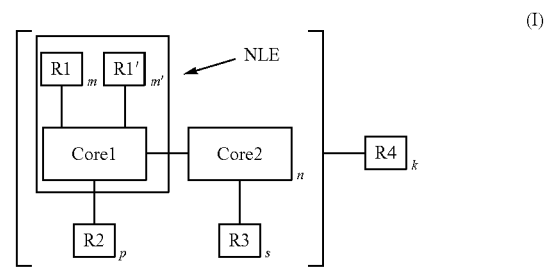

(I)

Core1 is an aromatic polycyclic conjugated molecule having two-dimensional flat form and self-assembles into supramolecular structures. R1 are electron donor groups connected to the aromatic polycyclic conjugated molecule (Core1) and R1' are electron acceptor groups connected to the aromatic polycyclic conjugated molecule (Core1), m is number of acceptor groups R1, m' is a number of donor groups R1', m and m' are equal to 0, 1, 2, 3, 4, 5 or 6, wherein m and m' are not both equal to 0, R2 is a substituent comprising one or more ionic groups from a class of ionic compounds that are used in ionic liquids connected to the aromatic polycyclic conjugated molecule (Core1) directly or via a connecting group, p is number of ionic groups R2 which is equal to 0, 1, 2, 3 or 4. The fragment marked NLE containing the Core1 with at least one group R1 and/or R1' has a nonlinear effect of polarization.

Core2 is an electro-conductive oligomer and number n of the electro-conductive oligomers is equal to 0, 2, or 4. R3 is a substituent comprising one or more ionic groups from a class of ionic compounds that are used in ionic liquids connected to the electro-conductive oligomer (Core2) directly or via a connecting group, s is number of the ionic groups R3 which is equal to 0, 1, 2, 3 or 4.

R4 is a resistive substituent connected to the aromatic polycyclic conjugated molecule (Core1) and/or to the electro-conductive oligomer (Core2) directly or via a connecting group. The resistive substituent R4 provides solubility of the organic compound in a solvent and electrically insulates the supramolecular structures from each other and. The parameter k is a number of substituents R4, which is equal to 1, 2, 3, 4, 5, 6, 7 or 8.

In one aspect, the present disclosure provides a solution comprising an organic solvent and at least one disclosed electro-polarizable compound.

In another aspect, the present disclosure provides a crystal metadielectric layer comprising a mixture of the electro-polarizable compounds as disclosed above. The nonlinearly polarizable fragments comprising an aromatic polycyclic conjugated molecule with at least one group R1 are placed into the resistive dielectric envelope formed by resistive substituents R4 providing solubility of the organic compound in a solvent and electrically insulating the supramolecular structures, such as supramolecular columns, from each other.

In still another aspect, the present disclosure provides a meta-capacitor comprising two metal electrodes positioned parallel to each other and which can be rolled or flat and planar with said metadielectric layer between said electrodes, wherein the metadielectric layer comprises one or more types of the disclosed electro-polarizable. The nonlinearly polarizable fragments comprising an aromatic polycyclic conjugated molecule with at least one group R1, the electro-conductive oligomers and the ionic groups which have electronic and/or ionic type of polarizability are placed into the resistive dielectric envelope formed by resistive substituents providing solubility of the organic compound in a solvent and electrically insulating the supramolecular structures from each other.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1A:
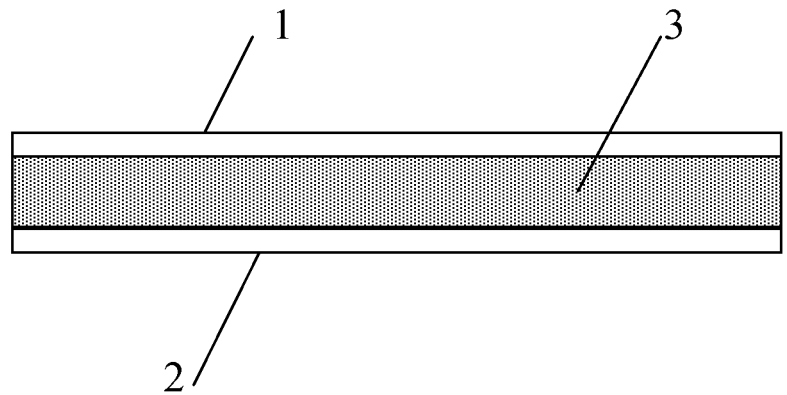
FIG. 1A schematically shows a capacitor with flat and planar electrodes in accordance with an aspect of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides an electro-polarizable compound. The existence of the electrophilic groups (acceptors) and the nucleophilic groups (donors) in an aromatic polycyclic conjugated molecule (Core1) promotes non-uniform distribution of electronic density in the conjugated molecule: surplus of electrons in one place (in a donor zone) and a shortage of electrons in other place (in an acceptor zone). The influence of external electric field onto non-uniform distribution of electronic density along the conjugated molecule leads to the induced polarization $P_{ind}$. In the general case the induced polarization is nonlinear function of intensity of local electric field $E_{loc}$. In the assumption of weak nonlinearity when it is possible to be limited to several members of decomposition of an induced polarization into a series on degrees of intensity of a local electric field, the induced polarization of the environment (of molecule) can be written down in the following form:

$$P_{ind} = \alpha \cdot E_{loc} + \beta \cdot E_{loc}^2 + \ldots,$$

where α-linear polarizability, β-square polarizability. Though the assumption of a smallness of electric field is not always right, nevertheless parameters α and β can be used for qualitative analysis of polarizability of the disclosed compounds. In the present disclosure the main attention is paid to ways of increase in the induced polarization of the disclosed compounds and therefore onto ways of increase of the linear polarizability α and square polarizability β. Such attention is caused by that the constant dipole and quadrupole electrical moments are mutually neutralized at self-assembly of such conjugated molecules. Analysis shows that linear polarizability depends on the size of the average electronic density in the molecule, and nonlinear polarizability depends on the size of heterogeneity of electronic density. It is also shown that a non-centrosymmetric arrangement of the electron donor and acceptor groups can lead to a strong nonlinear response of the compound's electronic polarization in the presence of an electric field. Influence of chemical structure on linear polarizability α and square polarizability β is shown in Table 1 below.

TABLE 1

| chemical structure | α (a.u.) | β (a.u.) |
|---|---|---|
| 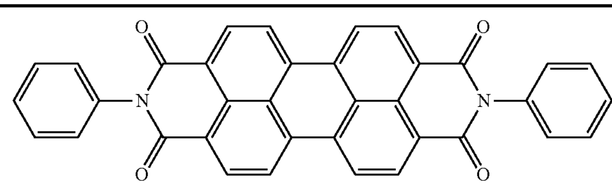 | 945 | 0.041 |

TABLE 1-continued

| chemical structure | α (a.u.) | β (a.u.) |
|---|---|---|
| [structure] | 1348 | 0.165 |
| [structure] | 1537 | 862 |
| [structure] | 1252 | 21107 |
| [structure] | 1908 | 40221 |
| [structure] | 1431 | 35189 |
| [structure] | 4604 | 1002570 |

An essential feature of the present disclosure is use of rigid non-conjugated limit carbon structures as resistive substituents. Such structures distinguish from the dielectric structures formed by "fat" tails (such as alkyl, aryl, substituted alkyl, substituted aryl, fluorinated alkyl, chlorinated alkyl, branched and complex alkyl) which can be bent (curved) and lead to stochastic distribution of electronic density in the dielectric structure that leads to its electric breakdown. Thus, as resistive substituent R4 is preferably a non-conjugated compound that minimizes or does not contain voids/empty space; that have dense packing of SP3 carbon with H and F substitutes. Otherwise use of fat tails may lead to formation of a friable dielectric structure (film, layer, and envelope). It is possible that in friable structure that there will be a local area ("hole") in which electronic density is equal to zero and which can be occupied with a free electron (that leads to electric breakdown). It is possible to enter a concept of a molecular hole when one molecule "is taken out" from the ordered structure (from a crystal lattice). In this case the quantum object (a quantum hole, a quantum point) is formed in which there are empty (non-occupied) energy levels. Set of such objects creates a condition for conductivity of electrons and for electric breakdown of dielectric structure.

Resistive substituents are preferentially selected from single and branched chains between 5 and 13 carbon-carbons in length in one direction and non-conjugated fused carbo-cyclic chains greater than 3 rings in length in one direction.

The presence of the electro-conductive oligomers leads to increasing polarizability of the disclosed electro-polarizable compound because of electronic super conductivity of the electro-conductive oligomers. The electro-conductive oligomer is selected from phenylene, thiophene, or substituted and/or unsubstituted polyacene quinine radical oligomer of lengths ranging from 2 to 12 or combination of two or more of these. Wherein the substitutions of ring hydrogens by O, S or NR5, and R5 is selected from the group consisting of unsubstituted or substituted $C_1$-$C_{18}$alkyl, unsubstituted or substituted $C_2$-$C_{18}$alkenyl, unsubstituted or substituted $C_2$-$C_{18}$alkynyl, and unsubstituted or substituted $C_4$-$C_{18}$ aryl. Ionic groups increase an ionic component of polarization of the disclosed electro-polarizable compound. The nonlinearly polarizable fragments comprising an aromatic polycyclic conjugated molecule with at least one dopant group, the electro-conductive oligomers and the ionic groups are placed into the resistive dielectric envelope formed by resistive substituents providing solubility of the organic compound in a solvent and electrically insulating the supra-molecular structures from each other. The resistive substituents increase the electric strength of these electro-polarizable compounds and breakdown voltage of the dielectric layers made on their basis.

In some implementations, among others, the aromatic polycyclic conjugated molecule (Core1) may comprise rylene fragments, which may be in conjugation with phenyl amides, naphthalene amides, and/or anthracene amides. In another embodiment of the disclosed electro-polarizable compound, the rylene fragments are selected from structures from 1 to 17 as given in Table 2.

TABLE 2

Examples of the aromatic polycyclic conjugated molecule comprising rylene fragments

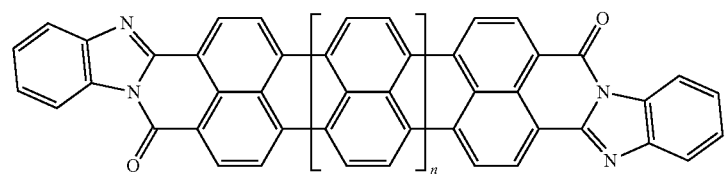

1

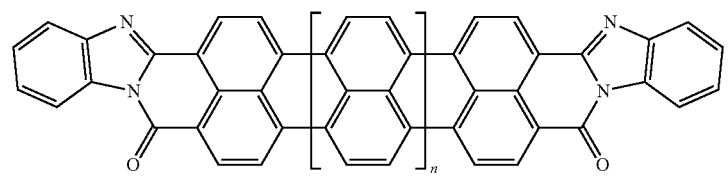

2

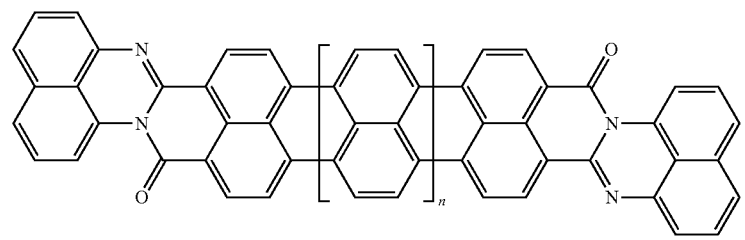

3

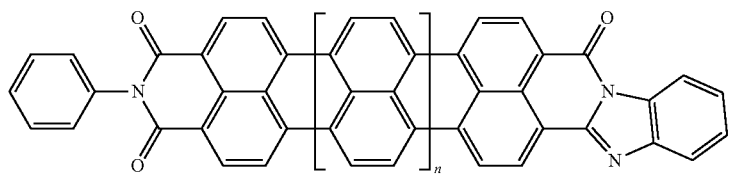

4

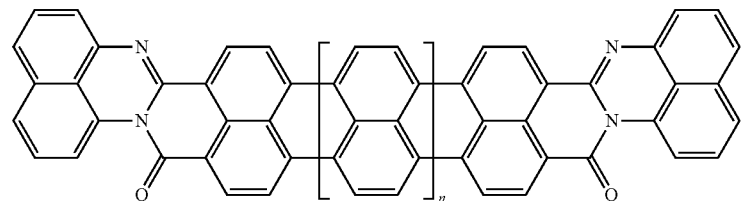

5

TABLE 2-continued
Examples of the aromatic polycyclic conjugated molecule comprising rylene fragments
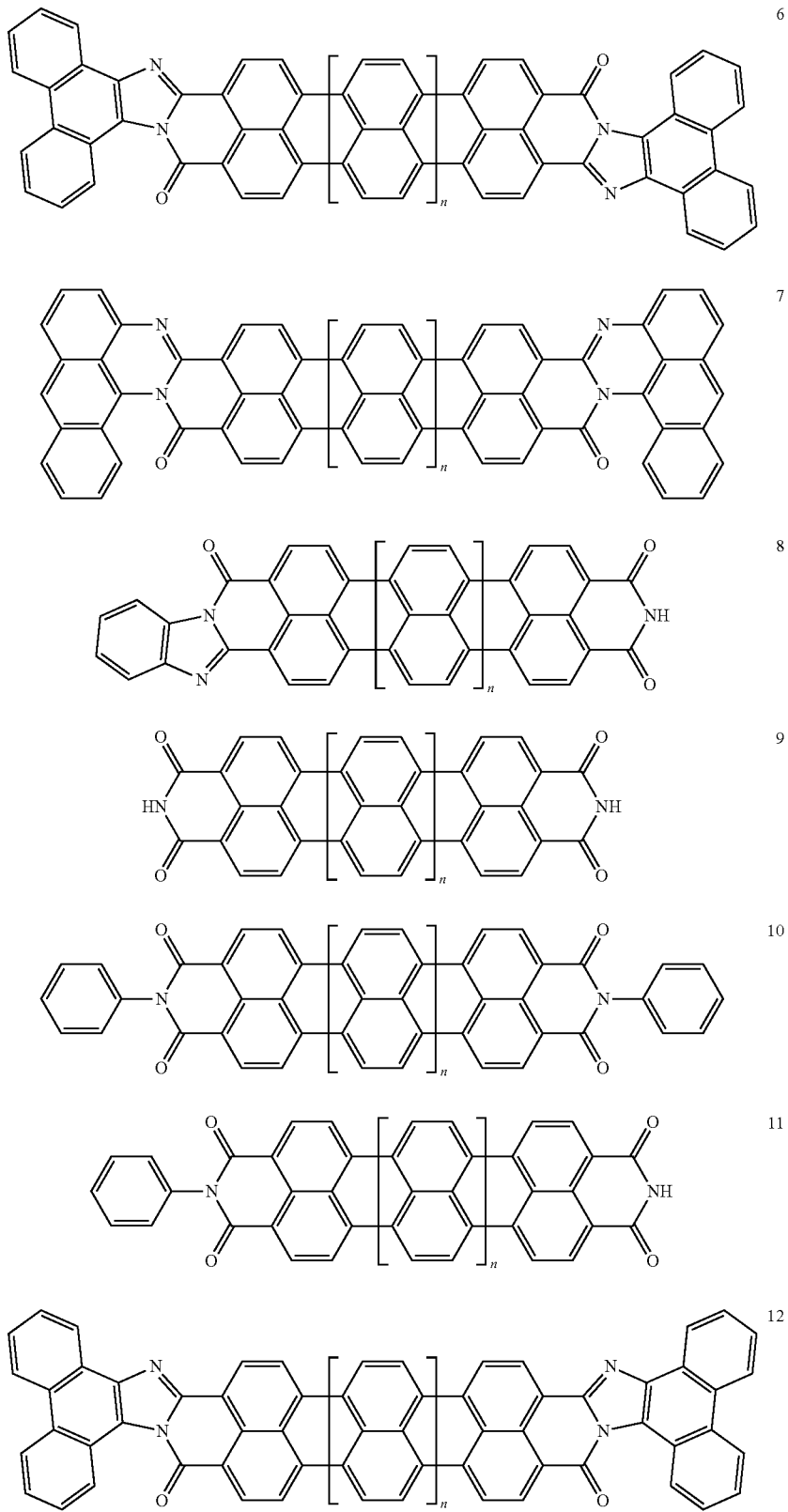

TABLE 2-continued
Examples of the aromatic polycyclic conjugated molecule comprising rylene fragments
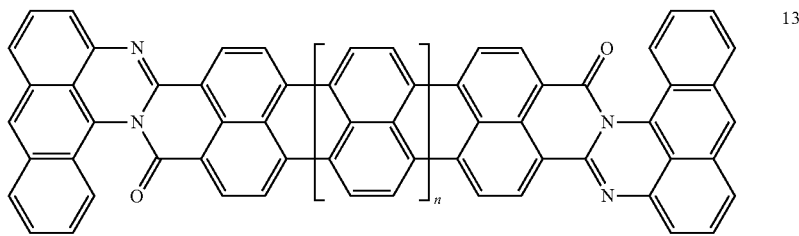
13
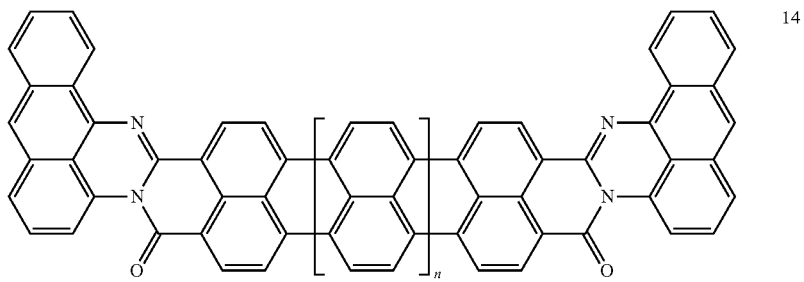
14
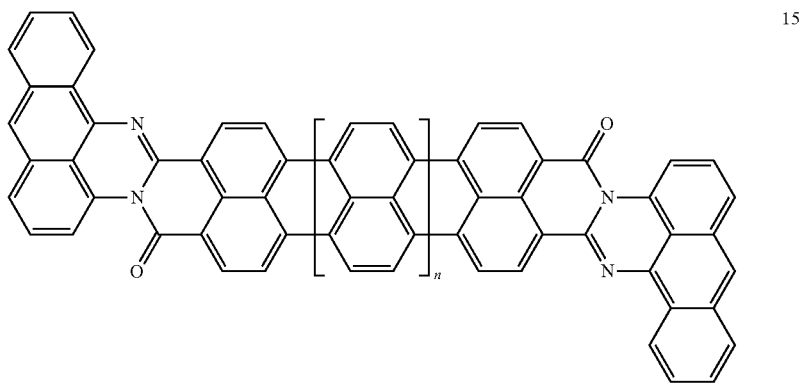
15
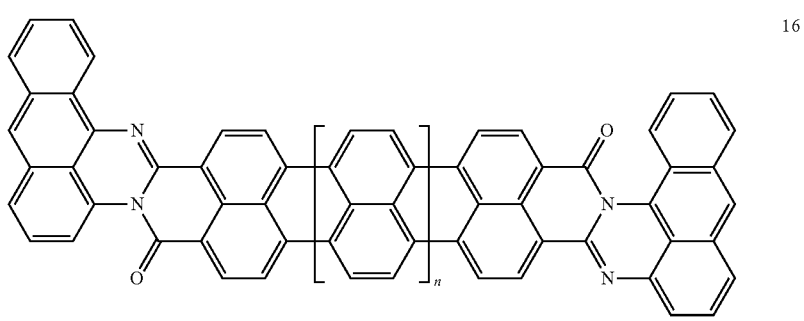
16
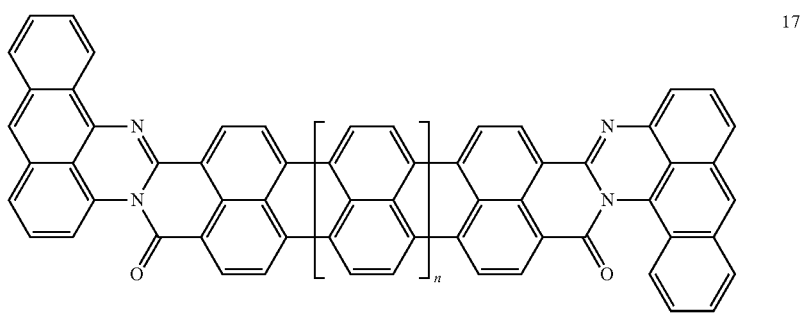
17

By way of example and not by way of limitation, the electron donor and acceptor groups (R1) may be selected from nucleophilic groups (donors) and electrophilic groups (acceptors) and the set (variety) of groups $(R1)_m$ containing of m elements comprises donors (R1') and/or acceptors (R1). The electrophilic groups (acceptors) are selected from —$NO_2$, —$NH_3+$ and —$NR_3+$(quaternary nitrogen salts), counterion $Cl^-$ or $Br^-$, —CHO (aldehyde), —CRO (keto group), —$SO_3H$ (sulfonic acids), —$SO_3R$ (sulfonates), —$SO_2NH_2$ (sulfonamides), —COOH (carboxylic acid), —COOR (esters, from carboxylic acid side), —COCl (carboxylic acid chlorides), —$CONH_2$ (amides, from carboxylic acid side), —$CF_3$, —$CCl_3$, —CN, —$C(CN)_2$ wherein R is radical selected from the list comprising alkyl (methyl, ethyl, iso-propyl, tert-butyl, neopentyl, cyclohexyl etc.), allyl (—$CH_2$—CH=$CH_2$), benzyl (—$CH_2C_6H_5$) groups, phenyl (+substituted phenyl) and other aryl (aromatic) groups. The nucleophilic groups (donors) are selected from —$O^-$ (phenoxides, like —ONa or —OK), —$NH_2$, —NHR, —$NR_2$, —OH, —OR (ethers), —NHCOR (amides, from amine side), —OCOR (esters, from alcohol side), alkyls, —$C_6H_5$, vinyls, wherein R is radical selected from the list comprising alkyl (methyl, ethyl, isopropyl, tert-butyl, neopentyl, cyclohexyl etc.), allyl (—$CH_2$—CH=$CH_2$), benzyl (—$CH_2C_6H_5$) groups, phenyl (+substituted phenyl) and other aryl (aromatic) groups.

Figure 2:
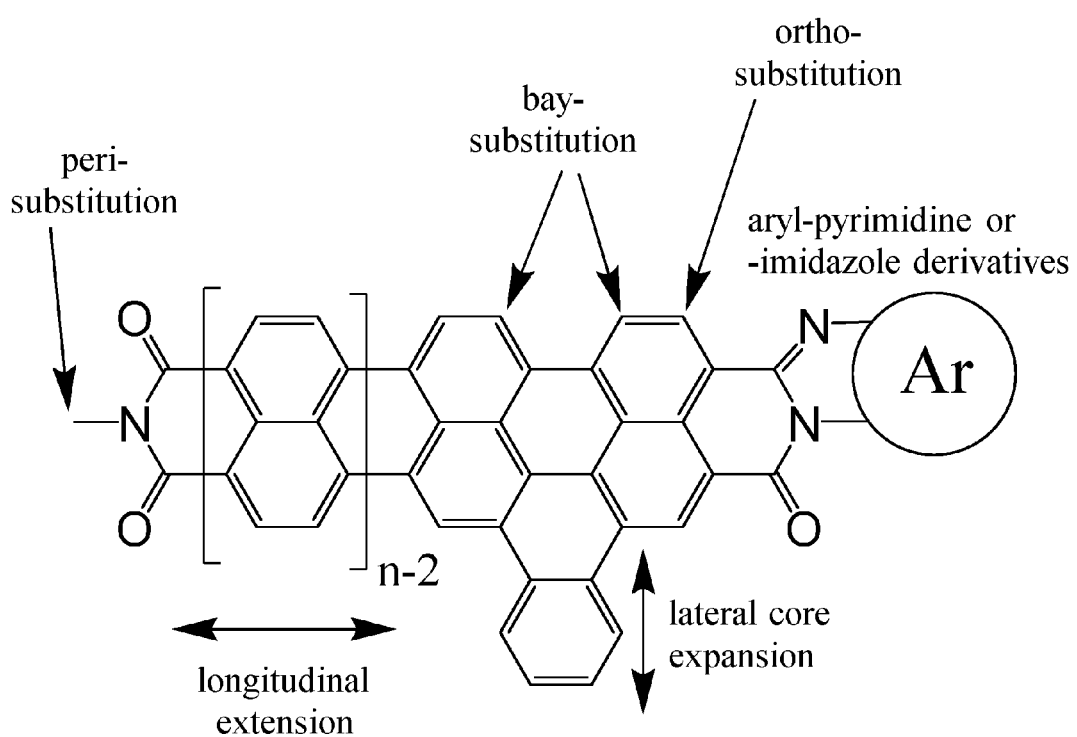
FIG. 2 shows a chemical formula that illustrates possible variations on a structure referred to as a rylene fragment that may be included in a Hein Electro-Polarizable compound in accordance with aspects of the present disclosure.

In another embodiment, the polycyclic aromatic Cores may be similarly expanded in the lateral dimension, herein defined as the direction that is in plane and perpendicular to the length wise dimension which is variable in compounds 1-17, which is herein defined as the longitudinal dimension. Such expansion is demonstrated in FIG. 2. Lateral expansion makes the Cores more planar and results in greater surface area for pi-pi interactions to enhance stacking effect. Lateral expansion also prevents the molecules from warping due to steric influences from neighboring molecules or substituents. These embodiments may still possess the electron donor and acceptor groups as described for compounds 1-17 and still possess the essential rigid non-conjugated limit carbon structures as resistive substituents. Some non-limiting examples of lateral expansion are shown below.

TABLE 3

Lateral Expansion Examples

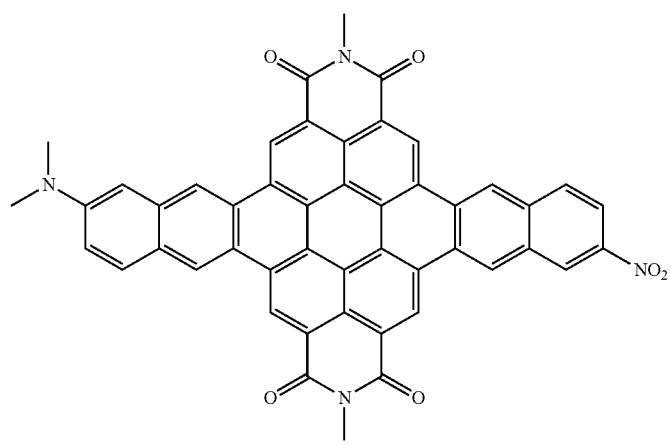 [SMILES: CN(C)c1ccc2cc3c(cc2c1)c1cc2c(=O)n(C)c(=O)c4cc5c6cc7ccc([N+](=O)[O-])cc7cc6c6cc7c(=O)n(C)c(=O)c8cc3c3c1c(c42)c5c6c3c87]

36

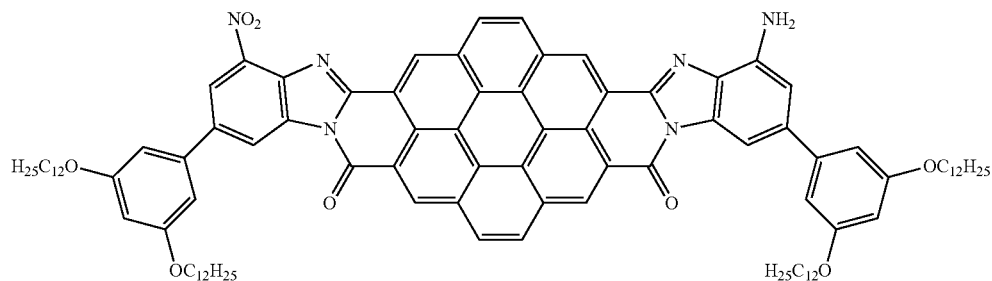

37

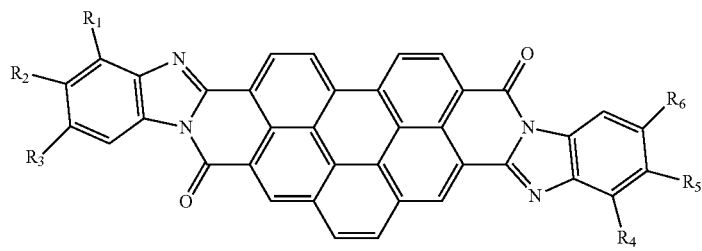

38

TABLE 3-continued

Lateral Expansion Examples

39

40

41

42

Wherein $R_1$, $R_2$, $R_3$, $R_4$, $R_5$, $R_6$ are each independently selected from hydrogen, electrophilic groups, nucleophilic groups, and resistive groups. In some embodiments, the resistive groups are connected via at least one connecting group.

In some implementations, the electro-polarizable compound may take the form of the following structure

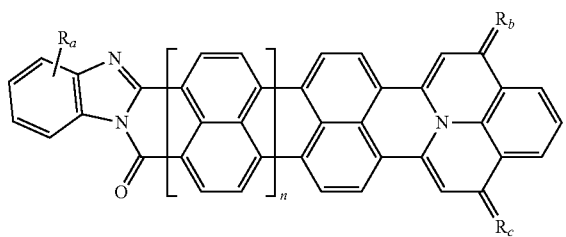

wherein $R_a$ is a nucleophile with or without alkyl resistive groups, and $R_b$ and $R_c$ are electrophilic groups. A non-limiting example of such a structure includes the structure

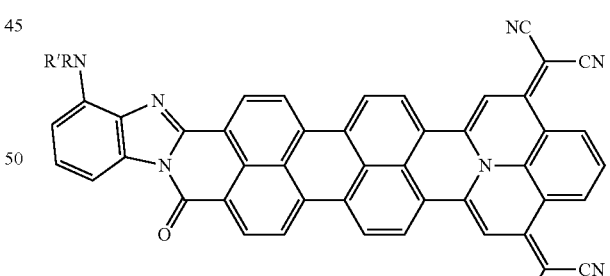

wherein R and R' are independently selected from hydrogen, and alkyl groups ranging between $C_1$-$C_{18}$.

In still another embodiment of the disclosed electro-polarizable compound, at least one connecting group is selected from the list comprising structures 18-35 given in Table 4, where X is hydrogen (H) or an alkyl group.

TABLE 4

| Examples of the conecting group | |
|---|---|
| (structure) | 18 |
| (structure) | 19 |
| (structure) | 20 |
| (structure) | 21 |
| (structure) | 22 |
| (structure) | 23 |
| (structure) | 24 |
| (structure) | 25 |
| (structure) | 26 |
| (structure) | 27 |
| (structure) | 28 |
| (structure) | 29 |
| (structure) | 30 |
| (structure) | 31 |

TABLE 4-continued

| Examples of the conecting group | |
|---|---|
| (structure) | 32 |
| (structure) | 33 |
| (structure) | 34 |
| (structure) | 35 |

In one embodiment of the present disclosure, the at least one connecting group is selected from the group of $CH_2$, $CF_2$, $SiR_2O$, $CH_2CH_2O$, wherein R is selected from the list comprising H, alkyl, and fluorine.

In yet another embodiment of the present disclosure, the resistive substituent R4 is selected from the group of alkyl, aryl, substituted alkyl, substituted aryl, fluorinated alkyl, chlorinated alkyl, branched and complex alkyl, branched and complex fluorinated alkyl, branched and complex chlorinated alkyl groups, and any combination thereof, and wherein the alkyl group is selected from methyl, ethyl, propyl, n-butyl, iso-butyl and tert-butyl groups, and the aryl group is selected from phenyl, benzyl and naphthyl groups or siloxane, and/or polyethylene glycol as linear or branched chains. In still another embodiment of the present disclosure, the resistive substituent R4 is $C_XQ_{2X+1}$, where $X \geq 1$ and Q is hydrogen (H), fluorine (F), or chlorine (Cl).

In one embodiment of the electro-polarizable compound, the aromatic polycyclic conjugated molecule (Core1) and the groups (R1) form a non-centrosymmetric molecular structure. In another embodiment of the electro-polarizable compound, the aromatic polycyclic conjugated molecule (Core1), the groups (R1) and the resistive substituents (R4) form a non-centrosymmetric molecular structure. In one embodiment of the present disclosure, the electro-polarizable compound has the following general formula (II):

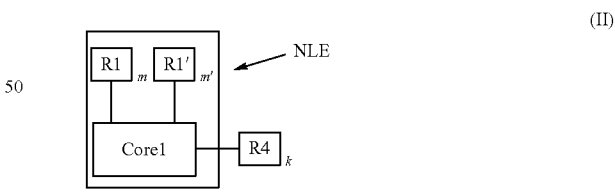

(II)

In general formula II, Core1 is the aromatic polycyclic conjugated molecule, as discussed above, the resistive substituent R4 is a non-conjugated part of disclosed compound, which may be saturated and fused cyclo-hydrocarbons or saturated and fused cyclo-halocarbons with rigid spatial structure including, but not limited to cyclohexane, cyclopentane, polycyclic perflourohexyls, polycyclic perflouropentyls, and structures that are built from tiles of cyclic carbon molecules. The tiles of cyclic carbon molecules may have dense packing of SP3 carbon saturated with H, F, Cl, or Br. In one particular implementation, parameters n=p=s=0. In another embodiment of the electro-polarizable compound, a length of the non-conjugated part is selected such that its resistivity is greater than $10^{15}$ ohm·cm. In yet another embodiment of the electro-polarizable compound, the resistive substituent R4 is selected from benzyl groups, benzyl alkoxy groups, benzyl halo-alkoxy groups, alkoxy groups, benzyl alkyl groups, benzyl halo-alkyl groups, alkyl groups, halo-alkoxy groups, halo-alkyl groups, benzyl aryl groups, and benzyl halo-aryl groups, wherein in the R4 substituents are connected to the apex of Core1 on which the nucleophilic groups (donor) R1 are connected, or the apex of Core1 on which the electrophilic group (acceptor) R1' is connected, but not both. In still another embodiment of the electro-polarizable compound, the resistive substituent R4 is resistive polycyclic substituents selected from the list comprising long $C_{25}H_{34}$ and $C_{25}H_{35}$ or $C_{25}F_{34}$ and $C_{25}F_{35}$ and located on the apex phenyl rings of Core1. In one embodiment of the present disclosure, the electro-polarizable compound has the following general formula (III):

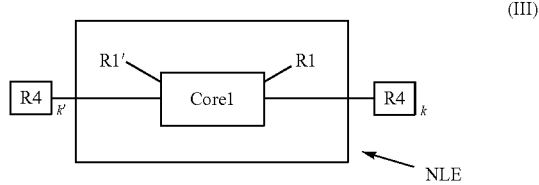

(III)

In general formula III, the parameters m and m' are equal to 1, R1' is an acceptor group, R1 is a donor group, k and k' indicate R4 resistive groups are on either end of the molecule. In another embodiment of the electro-polarizable compound, the Core1 is rylene fragment having the following structural formula where repetition parameter t is an integer varying from 0 to 5:

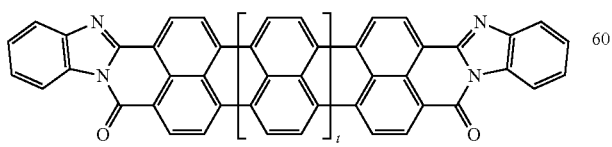

wherein the set of the electron donor and acceptor groups comprises one donor group —$NEt_2$ and one acceptor groups —$NO_2$ (m and m' are both equal to 1) located on rylene phenyl rings and/or apex phenyl ring positions of the Core1, so that the fragment having a nonlinear effect of polarization (NLE) is represented by the following chemical structure (when t=0):

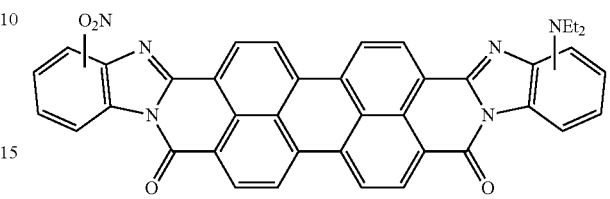

wherein the resistive substituents (R4) are benzyl alkoxy groups and in some instances are attached via a benzyl group such as:

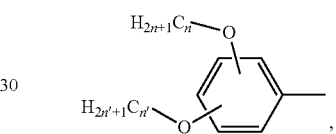

wherein n and n' range from 4-25. This leads to the following structural formula (IV):

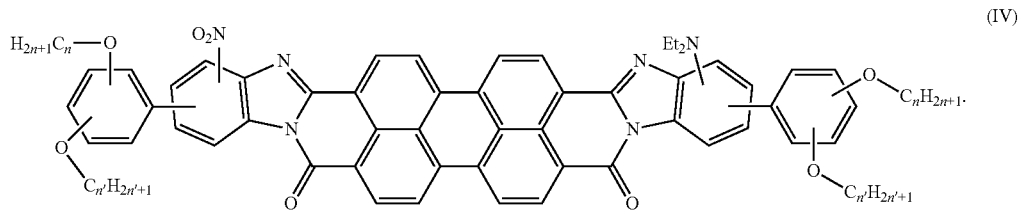

(IV)

In some embodiments resistive substituents (R4) are branched alkyl or alkoxy groups attached via an alkyne connecting group, for example:

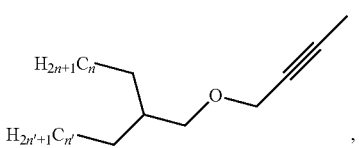

wherein n and n' range from 4-25. This leads to the following structural formula (V):

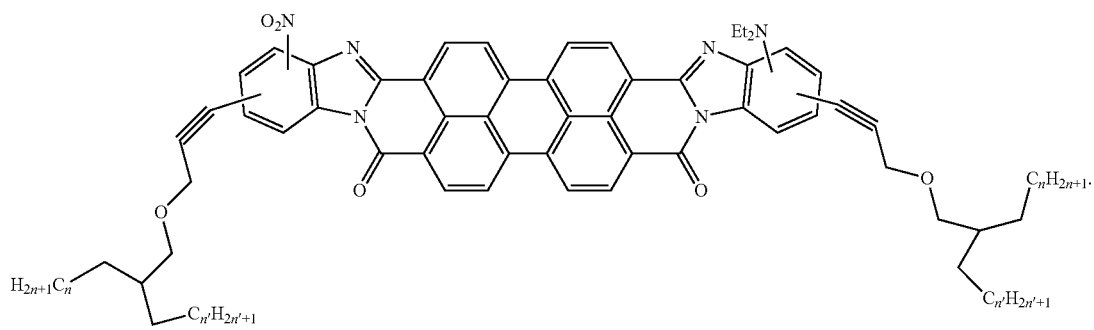

(V)

In another embodiment of the present disclosure, the electro-polarizable compound has the following general formula (VI):

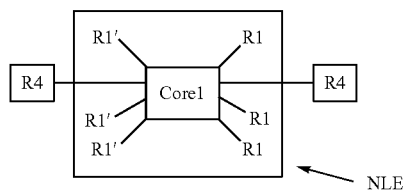

(VI)

In general formula VI, Core1 is the above-described aromatic polycyclic conjugated molecule, m is equal to 6, R1' is donor group, R1 is acceptor group, k is equal to 2. In yet another embodiment of the electro-polarizable compound, the Core1 is rylene fragment having the following structural formula where repetition parameter t varies from 1 to 5:

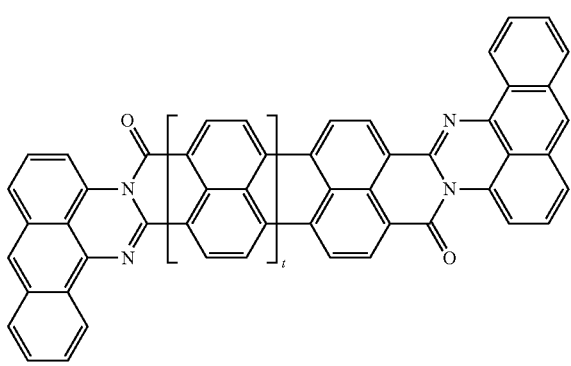

wherein the set of the electron donor and acceptor groups comprises three donor groups —$NH_2$ and three acceptor groups —$NO_2$ (m is equal to 6) are located on rylene phenyl rings and/or apex phenyl ring positions of the Core1, so that the fragment having a nonlinear effect of polarization (NLE) is represented by following chemical structure (when t=1):

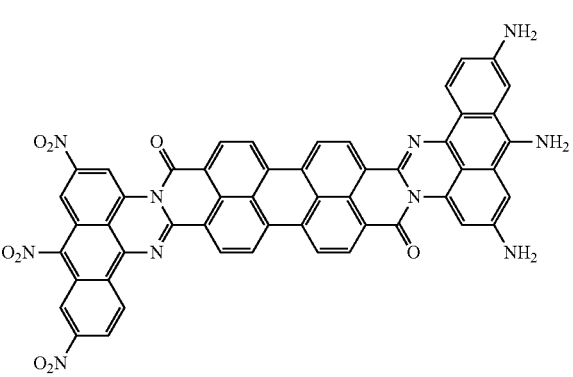 [SMILES: Nc1ccc2c(c1)c(N)c1cc(N)cc3c1c2nc1c2ccc4c5ccc6c(=O)n7c8cc([N+](=O)[O-])cc9c([N+](=O)[O-])c%10cc([N+](=O)[O-])ccc%10c(nc7c7ccc(c%10ccc(c(=O)n31)c2c4%10)c5c67)c98]

wherein the resistive substituent (R4) is an amine structure of the following type:

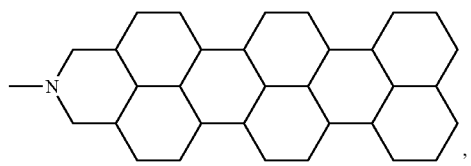 [SMILES: CN1CC2CCC3C4CCC5C6CCCC7CCCC(C8CCC(C9CCC(C1)C2C39)C4C58)C76]

leading to the following structural formula (VII):

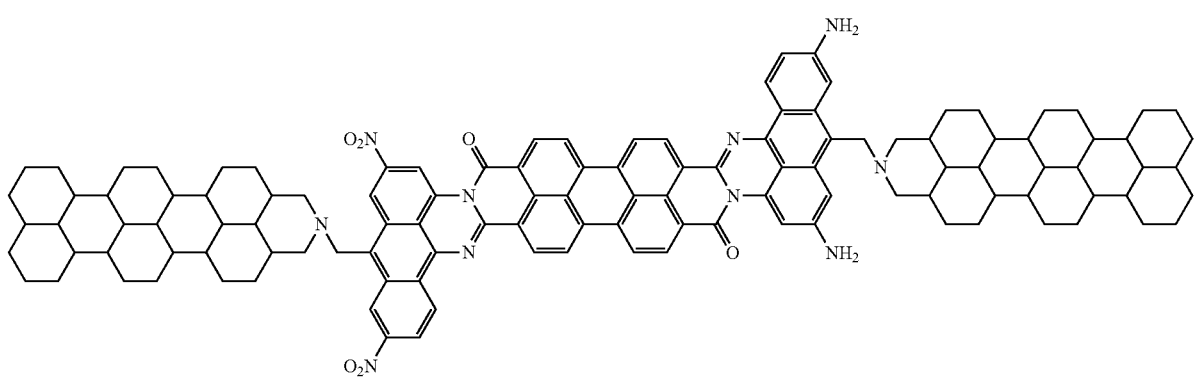

(VII)

wherein the resistive substituents are connected via a connecting group.

Non-limiting examples of the electro-polarizable cores includes at least two regioisomers selected from the below structures:

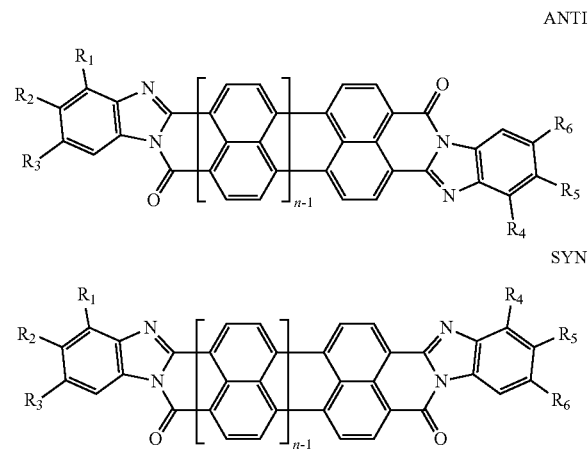

ANTI

SYN wherein $R_1$, $R_2$, $R_3$, $R_4$, $R_5$, $R_6$ are each independently selected from hydrogen, electrophilic groups, nucleophilic groups, and resistive groups; and n is an integer greater than or equal to 1. Non-limiting examples of such combinations of substituents are listed in Table 5.

| Conf. | n | $R_1$ | $R_2$ | $R_3$ | $R_4$ | $R_5$ | $R_6$ |
|---|---|---|---|---|---|---|---|
| ANTI | 2 | H | $NH_2$ | H | H | $NO_2$ | H |
| ANTI | 2 | H | $NH_2$ | H | H | $NO_2$ | $NO_2$ |
| ANTI | 2 | H | $NO_2$ | $NH_2$ | H | $NH_2$ | $NO_2$ |
| ANTI | 2 | $NH_2$ | H | DB | $NO_2$ | H | DB |
| SYN | 2 | $NH_2$ | H | DB | $NO_2$ | H | DB |
| ANTI | 3 | $NH_2$ | H | DB | $NO_2$ | H | DB |
| SYN | 3 | $NH_2$ | H | DB | $NO_2$ | H | DB |
| ANTI | 4 | $NH_2$ | H | DB | $NO_2$ | H | DB |
| SYN | 4 | $NH_2$ | H | DB | $NO_2$ | H | DB |
| ANTI | 2 | NRR' | H | DB | $NO_2$ | H | DB |
| SYN | 2 | NRR' | H | DB | $NO_2$ | H | DB |

Wherein R and R' can be the same or independently selected from alkyl, alkene, and substituted alkyl groups; and wherein DB is 3,5-dimethoxyphenyl. The electro-polarizable compounds may be further modified to include resistive substituents connected to the core via DB groups, or connecting groups listed in Table 4.

In some embodiments, a dielectric layer of electro-polarizable compounds is comprised of more than one regioisomer. In some embodiments, a dielectric layer comprised of electro-polarizable compounds includes a mixture of electro-polarizable compounds.

In one embodiment of the present disclosure, the induced polarization $P_{ind}$ of the electro-polarizable compound may be written in the form of decomposition into a series on degrees of intensity of a local electric field $E_{loc}$:

$$P_{ind} = \alpha \cdot E_{loc} + \beta \cdot E_{loc}^2 + \ldots,$$

where $\alpha$ represents linear polarizability, $\beta$ represents square polarizability.

In an aspect, the present disclosure provides the organic solvent comprising the disclosed electro-polarizable compound. In one embodiment, the solution comprises a mixture of different electro-polarizable compounds. In another embodiment of the disclosed organic solvent, the mixture of the electro-polarizable compounds comprises the rylene fragments of different length. In still another embodiment, the organic solvent is selected from the list comprising ketones, carboxylic acids, hydrocarbons, cyclic hydrocarbons, chlorohydrocarbons, alcohols, ethers, esters, and any combination thereof. In yet another, the organic solvent is selected from the list comprising acetone, xylene, toluene, ethanol, methylcyclohexane, ethyl acetate, diethyl ether, octane, chloroform, methylene chloride, dichloroethane, trichloroethene, tetrachloroethene, carbon tetrachloride, 1,4-dioxane, tetrahydrofuran, pyridine, triethylamine, nitromethane, acetonitrile, dimethylformamide, dimethyl sulfoxide, and any combination thereof. In yet another embodiment of disclose, the solution is a lyotropic liquid crystal solution.

In another aspect, aspects of the present disclosure provide a crystal metadielectric layer comprising at least one type of the disclosed electro-polarizable compounds. The crystal metadielectric layers are produced from the disclosed organic compound by Cascade Crystallization; a method of thin crystal film (or thin crystal layer) manufacturing known as the Optiva-Process. See U.S. Pat. Nos. 5,739,296 and 6,049,428, and P. Lazarev et al., "X-ray Diffraction by Large Area Organic Crystalline Nano-films", Molecular Materials, 14 (4), 303-311 (2001), and Bobrov, "Spectral Properties of Thin Crystal Film Polarizers", Molecular Materials, 14 (3), 191-203 (2001).

Cascade Crystallization process involves a chemical modification step and four steps of ordering during the crystal metadielectric layer formation. The chemical modification step introduces hydrophilic groups on the periphery of the molecule of the disclosed organic compound in order to impart amphiphilic properties to the molecule. Amphiphilic molecules stack together into supramolecular structures, which is the first step of ordering. At certain concentration, supramolecular structures are converted into a liquid-crystalline state to form a lyotropic liquid crystal, which is the second step of ordering. The lyotropic liquid crystal is deposited under the action of a shear force (or meniscus force) onto a substrate based on a Mayer Rod shearing technique, so that shear force (or the meniscus) direction determines the crystal axis direction in the resulting solid crystal layer. The external alignment upon the lyotropic liquid crystal can be produced using any other means, for example by applying an external electric field at normal or elevated temperature, with or without additional illumination, magnetic field, or optical field (e.g., coherent photovoltaic effect); the degree of the external alignment should be sufficient to impart necessary orientation to the supramolecular structures of the lyotropic liquid crystal and form a structure, which serves as a base of the crystal lattice of the dielectric layer. This directional deposition is third step of ordering, representing the global ordering of the crystalline or polycrystalline structure on the substrate surface. The last fourth step of the Cascade Crystallization process is drying/crystallization, which converts the lyotropic liquid crystal into a solid crystal dielectric layer. The term Cascade Crystallization process is used to refer to the chemical modification and four ordering steps as a combination process.

The Cascade Crystallization process is used for production of thin crystalline metadielectric layers. The dielectric layer produced by the Cascade Crystallization process has a global order which means that a direction of the crystallographic axis of the layer over the entire substrate surface is controlled by the deposition process. Molecules of the deposited material are packed into supramolecular structures with a limited freedom of diffusion or motion. The thin crystalline dielectric layer is characterized by an interplanar spacing of 3.4±0.3 Angstroms (Å) in the direction of one of the optical axes.

In one embodiment of the present disclosure, the crystal metadielectric layer comprises supramolecular structures such as columns, needles, etc., formed by the electro-polarizable compounds comprising the rylene fragments of different length. The variety of the rylene fragment lengths increases the randomness of the stack. In one embodiment according to aspects of the present disclosure, the layer's relative permittivity is greater than or equal to 1000. In one embodiment, the real part of the relative permittivity ($\varepsilon'$) of the crystal metadielectric layer comprises first-order ($\varepsilon^{(1)}$) and second-order ($\varepsilon^{(2)}$) permittivities according to follow formula:

$$\varepsilon' = \varepsilon^{(1)} + 2\varepsilon^{(2)} \frac{V_0}{d},$$

where $V_0$ is the DC-voltage which is applied to the crystal metadielectric layer, d is the layer thickness. In another embodiment of the present invention, the layer's resistivity is greater than or equal to $10^{13}$ ohm/cm.

The present disclosure provides the metacapacitor comprising two metal electrodes positioned parallel to each other and which can be rolled or flat and planar and metadielectric layer between said electrodes. The layer comprises the electro-polarizable compounds as disclosed above.

The metacapacitor comprises a first electrode 1, a second electrode 2, and a metadielectric layer 3 disposed between said first and second electrodes as shown in FIG. 1A. The electrodes 1 and 2 may be made of a metal, such as copper, zinc, or aluminum or other conductive material such as graphite or carbon nanomaterials and are generally planar in shape.

The electrodes 1, 2 may be flat and planar and positioned parallel to each other. Alternatively, the electrodes may be planar and parallel, but not necessarily flat, they may be coiled, rolled, bent, folded, or otherwise shaped to reduce the overall form factor of the capacitor. It is also possible for the electrodes to be non-flat, non-planar, or non-parallel or some combination of two or more of these. By way of example and not by way of limitation, a spacing d between the electrodes 1 and 2 may range from about 100 nm to about 10,000 μm. The maximum voltage $V_{bd}$ between the electrodes 1 and 2 is approximately the product of the breakdown field $E_{bd}$ and the electrode spacing d. If $E_{bd}$=0.1 V/nm and the spacing d between the electrodes 1 and 2 is 10,000 microns (100,000 nm), the maximum voltage $V_{bd}$ would be 100,000 volts.

The electrodes 1 and 2 may have the same shape as each other, the same dimensions, and the same area A. By way of example, and not by way of limitation, the area A of each electrode 1 and 2 may range from about 0.01 m² to about 1000 m². By way of example and not by way of limitation for rolled capacitors, electrodes up to, e.g., 1000 m long and 1 m wide.

These ranges are non-limiting. Other ranges of the electrode spacing d and area A are within the scope of the aspects of the present disclosure.

If the spacing d is small compared to the characteristic linear dimensions of electrodes (e.g., length and/or width), the capacitance C of the capacitor may be approximated by the formula:

$$C = \varepsilon \varepsilon_o A/d, \qquad (V)$$

where $\varepsilon_0$ is the permittivity of free space (8.85×10⁻¹² Coulombs²/(Newton·meter²)) and ε is the dielectric constant of the dielectric layer. The energy storage capacity U of the capacitor may be approximated as:

$$U = \tfrac{1}{2} \varepsilon \varepsilon_o A E_{bd}^2 d \qquad (VI)$$

The energy storage capacity U is determined by the dielectric constant ε, the area A, and the breakdown field $E_{bd}$. By appropriate engineering, a capacitor or capacitor bank may be designed to have any desired energy storage capacity U. By way of example, and not by way of limitation, given the above ranges for the dielectric constant ε, electrode area A, and breakdown field $E_{bd}$ a capacitor in accordance with aspects of the present disclosure may have an energy storage capacity U ranging from about 500 Joules to about 2·10¹⁶ Joules.

For a dielectric constant ε ranging, e.g., from about 100 to about 1,000,000 and constant breakdown field $E_{bd}$ between, e.g., about 0.1 and 0.5 V/nm, a capacitor of the type described herein may have a specific energy capacity per unit mass ranging from about 10 W·h/kg up to about 100,000 W·h/kg, though implementations are not so limited.

Figure 1B:
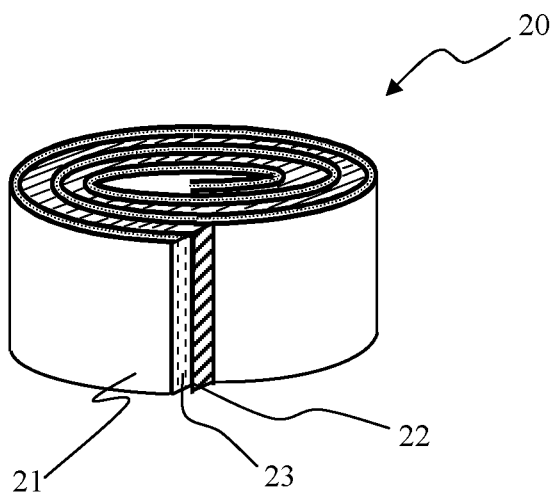
FIG. 1B schematically shows a capacitor with rolled (circular) electrodes in accordance with another aspect of the present disclosure.

The present disclosure includes metacapacitors that are coiled, e.g., as depicted in FIG. 1B. In this example, a metacapacitor 20 comprises a first electrode 21, a second electrode 22, and a metadielectric material layer 23 of the type described hereinabove disposed between said first and second electrodes. The electrodes 21 and 22 may be made of a metal, such as copper, zinc, or aluminum or other conductive material such as graphite or carbon nanomaterials and are generally planar in shape. In one implementation, the electrodes and metadielectric material layer 23 are in the form of long strips of material that are sandwiched together and wound into a coil along with an insulating material, e.g., a plastic film such as polypropylene or polyester to prevent electrical shorting between the electrodes 21 and 22.

In order that the invention may be more readily understood, reference is made to the following examples, which are intended to be illustrative of the invention, but are not intended to limit its scope.

Example 1

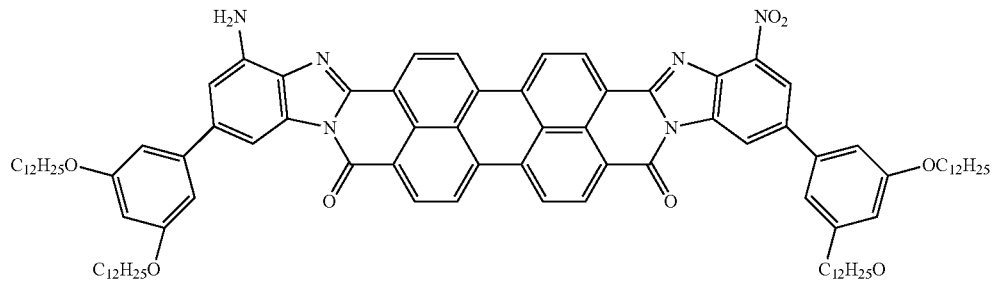

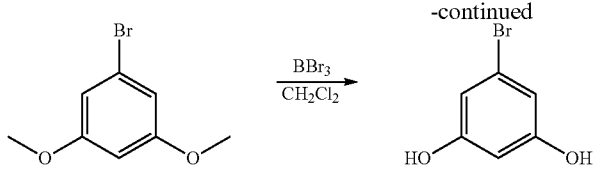

Synthesis of 3,5-dihydroxybromobenzene

To a reaction flask oven dried overnight at 90° C., 3,5-dimethoxybromobenzene (1 eq.) was dissolved in anhydrous $CH_2Cl_2$ and placed in an ice water bath to cool for 10 minutes. To this chilled solution, $BBr_3$ (1M in $CH_2Cl_2$, 2.2 eq.) was slowly added over 5 minutes. Once this addition was complete, the reaction was removed from the ice water bath and allowed to warm in air to room temperature and allowed to stir overnight. The reaction was confirmed to be completed after 18 hours by $SiO_2$ TLC using 1:1 Hexanes: EtOAc. The reaction was placed back on an ice water bath to cool for 10 minutes before 1 mL of methanol was added to quench any unreacted $BBr_3$ still present. This reaction mixture was washed with aqueous HCl (2 M) and extracted with EtOAc (3×). The organic fractions were collected and dried with $Na_2SO_3$ before being filtered. The crude reaction mixture was concentrated under vacuum and precipitated into hexanes to yield 3,5-dihydroxybromobenzene.

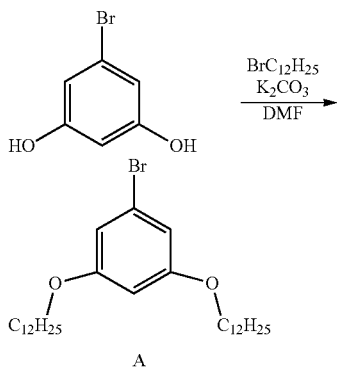

Synthesis of A:

To reaction flask oven dried overnight at 90° C., 3,5-dihydroxybromobenzene (1 eq.) and $K_2CO_3$ (3 eq.) was dissolved in anhydrous DMF and stirred at room temperature for 10 minutes. To this mixture, bromododecane (3 eq.) was added and the reaction was placed in a preheated 100° C. oil bath and stirred overnight. The reaction was confirmed to be completed after 18 hours by $SiO_2$ TLC using 1:1 Hexanes: EtOAc. The reaction removed from the oil bath and allowed to cool in air to room temperature. Excess $K_2CO_3$ was quenched with aqueous HCl (2 M) and the reaction was extracted with EtOAc. The organic fractions were collected, washed with deionized water and dried with $Na_2SO_3$ before being filtered. The solvent was removed under vacuum and the product was purified by silica gel chromatography (100% Hexanes to 10% EtOAc:90% Hexanes) and isolated as a colorless oil that slowly solidified into a white solid.

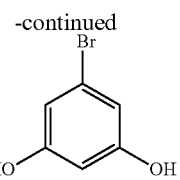

Synthesis of B:

A (1 eq.), bis(pinacolato)diboron (1.6 eq.), potassium acetate (3 eq.), $Pd(dppf)Cl_2$ (0.03 eq.) were evacuated inside a 100 mL round bottom flask and backfilled with $N_2$. In a separate flask, dioxane was sparged under a $N_2$ flow for 15 min before being added to the reaction flask via syringe. This reaction solution was placed in a preheated oil bath set to 90° C. and monitored by TLC (9:1 Hexanes: EtOAc). When the reaction was complete, the reaction mixture was washed with 2M HCl and extracted with ethyl acetate. The organic fractions were collected and dried using $Na_2SO_4$ and filtered before removing the solvent under reduced pressure. The crude material was re-dissolved in hexanes and filtered using a silica plug using hexanes as the eluent. Hexane was removed under reduced pressure to isolate a viscous oil. This crude mixture stirred for 1 h in methanol to give a white solid precipitate that was collected by vacuum filtration. B was isolated as a white solid.

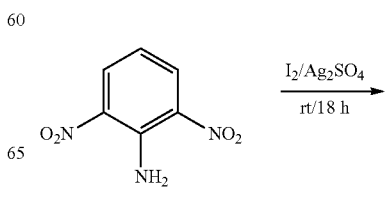

-continued

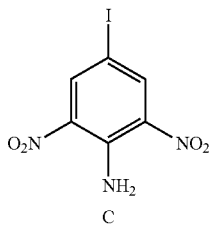
C

Synthesis of C:

2,6-dinitroaniline (1 eq.), Ag$_2$SO$_4$ (1.4 eq.), and I$_2$ (1.4 eq) were added to a 50 mL round bottom flask at room temperature. To this mixture, ethanol was added and the reaction was allowed to stir at room temperature for 18 hours. The next morning a yellow precipitate had formed and TLC analysis (1:1 EtOAc:Hexanes) had shown complete consumption of the starting material. This reaction mixture was filtered, and the solid residue was washed with EtOAc until the filtrate ran clear. The solvent was then removed from the filtrate under vacuum and the crude solid was re-dissolved in a minimum amount of CH$_2$Cl$_2$ before being precipitated into of hexanes. The mixture was set aside for 30 minutes until no more solid precipitated and the solid was isolated via vacuum filtration. C was isolated as an orange solid.

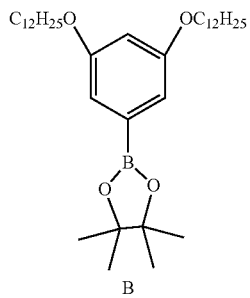
B

+

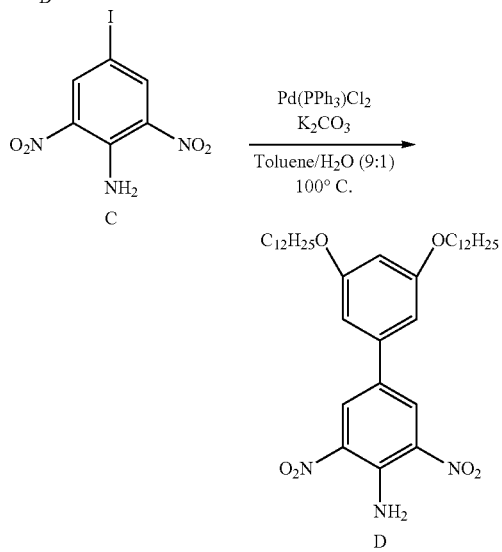

Synthesis of D:

C (1 eq.), B (1.1 eq.), Pd(PPh$_3$)$_2$Cl$_2$ (0.03 eq.), and K$_2$CO$_3$ (2 eq.) were added to a 25 mL round bottom flask before being evacuated and backfilled with N$_2$ three times. In a separate flask, N$_2$ was bubbled through a solution of toluene and H$_2$O for 30 min before adding this solution to the reaction flask. This solution was then placed in a preheated oil bath at 100° C. and stirred for overnight. The reaction was monitored by TLC (7:3 Hexanes:EtOAc). Once the reaction was complete, it was removed from the oil bath and allowed to cool to room temperature in air for 30 min. The mixture was washed distilled water and excess base was carefully acidified with the addition of 2M HCl then extracted with EtOAc. The organic fractions were collected and dried with NaSO$_4$, filtered, and the solvent was removed under vacuum distillation. The crude product was dissolved in a minimum amount of CH$_2$Cl$_2$ and precipitated into MeOH. The solid was filtered to give D as a yellow solid.

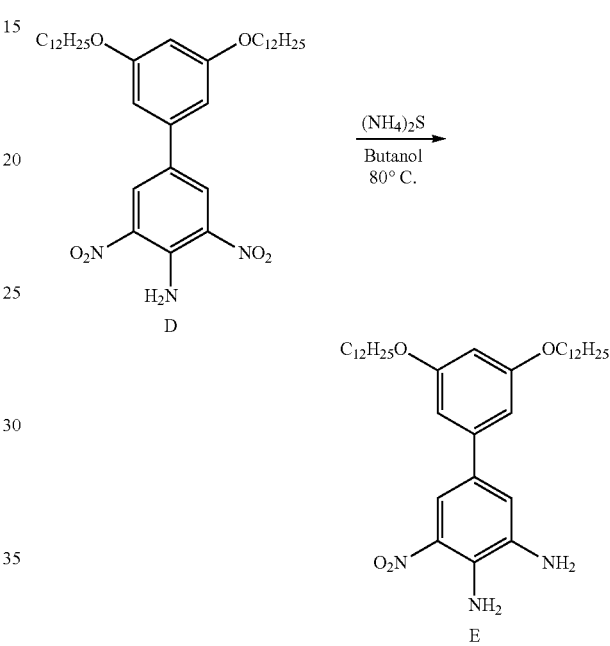

Synthesis of E:

D (1 eq.), was added to a round bottom flask and dissolved into n-butanol at 80° C. To this solution was added a 20 wt % aqueous solution of (NH$_4$)$_2$S (2 eq.). The reaction was stirred for 1 hour and was monitored by TLC (7:3 Hexanes/EtOAc). When the reaction was complete, the reaction mixture was washed with 2 M HCl and extracted with ethyl acetate. The organic fractions were collected and dried using Na$_2$SO$_4$ and filtered before removing the solvent under reduced pressure. The crude material was re-dissolved in hexanes purified using SiO$_2$ column chromatography (7:3 Hexanes/EtOAc) to give E as a viscous red oil.

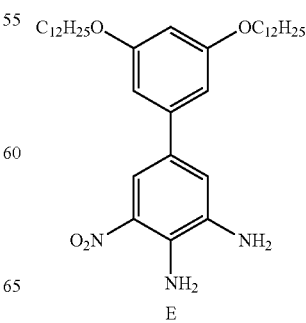

+

-continued

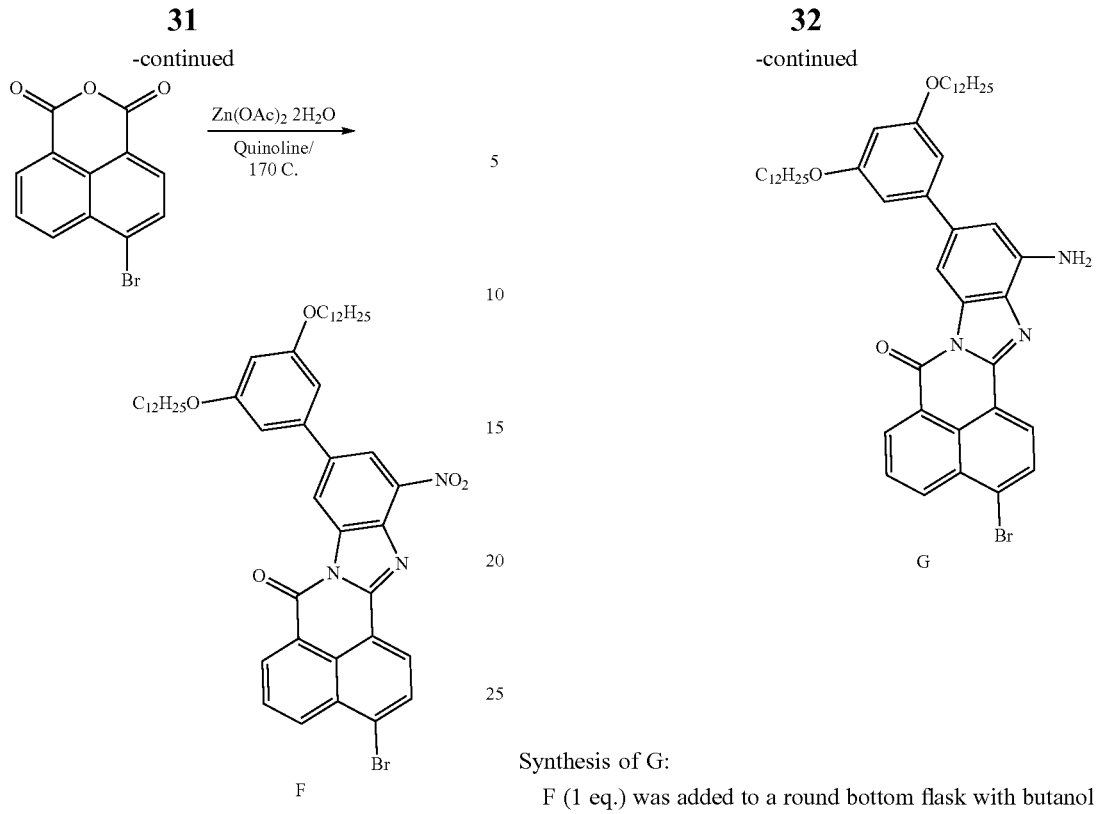

Synthesis of F:

E (1 eq.) and 4-bromonaphthalic anhydride (1.2 eq), and Zn(OAc)$_2$ 2H$_2$O (0.4 eq.) were added to a round bottom flask before being evacuated and backfilled with N$_2$. In a separate flask, quinoline was purged for 15 min under a flow of N$_2$ and added to the reaction mixture. This suspension was heated to 170° C. and let to stir overnight. When the reaction is complete, the hot solution was poured into MeOH and the resulting solid was washed with 20 mL of additional MeOH before being collected. Residual MeOH was removed under reduced pressure to give F.

Synthesis of G:

F (1 eq.) was added to a round bottom flask with butanol (0.3 M). This suspension was heated to 80° C. and a reducing agent (SnCl$_2$, (NH$_4$)$_2$S, or HNaS; 1 eq.) was transferred to the hot reaction mixture. The reaction was monitored by TLC analysis and allowed to stir overnight. When the reaction was complete, the reaction mixture was diluted with water and extracted with ethyl acetate. The organic fractions were collected and dried using Na$_2$SO$_4$ and filtered before removing the solvent under reduced pressure. The crude material was re-dissolved in hexanes purified using SiO$_2$ column chromatography (Hexanes/EtOAc, then EtOAc) to give G.

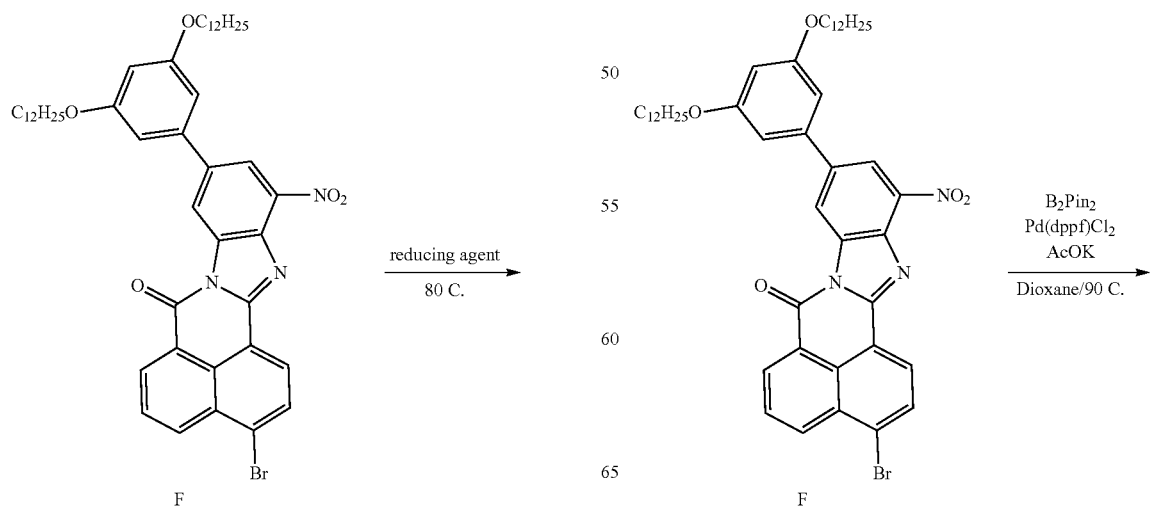

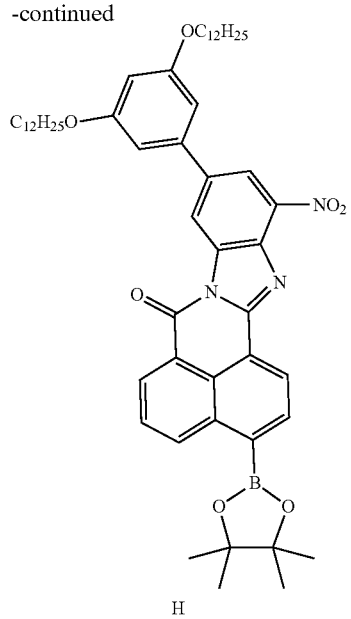

H

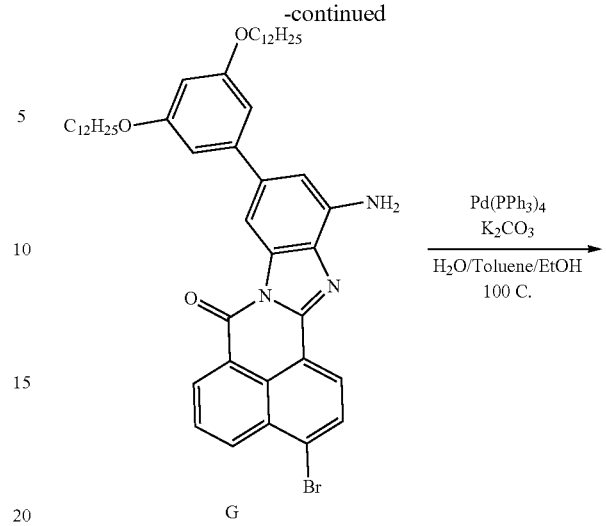

G

Synthesis of H:

F (1 eq.), Pd(dppf)Cl$_2$ (0.05 eq.), AcOK (2 equiv.), and B$_2$Pin$_2$ (1.5 eq.) were added to 25 mL round bottom flask. This mixture was then evacuated and backfilled with N$_2$ 3 times. In a separate flask, dioxane (0.3 M) was bubbled with N$_2$ for 30 minutes. This degassed solvent was then added to the reaction flask under an N$_2$ atmosphere and placed into a preheated 100° C. oil bath and allowed to stir overnight. When the reaction was complete, it was removed from the oil bath and allowed to cool to room temperature before being washed with 2M HCl and extracted using EtOAc. The organic layers were collected, dried with Na$_2$SO$_4$, filtered, and the solvent was removed under reduced pressure. The crude product was purified by column chromatography (100% Hexanes-8:2 Hexanes/EtOAc). The solvent was removed to give H.

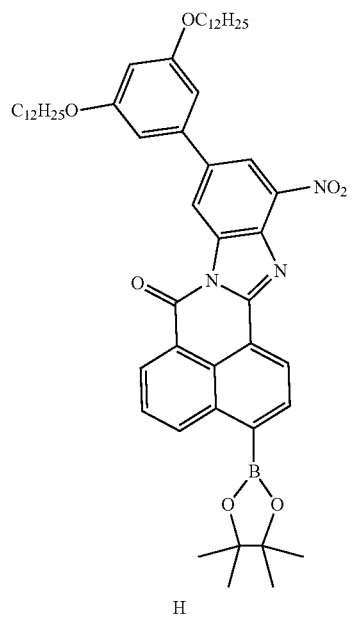

H

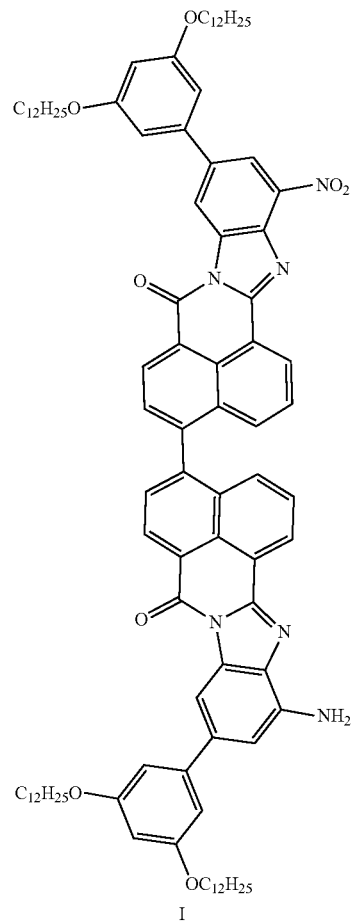

I

Synthesis of I:

H (1 eq.), Pd(PPh$_3$)$_4$ (0.05 eq.), K$_2$CO$_3$ (2 eq.), and G (1 eq.) were added to a reaction flask. This mixture was then evacuated and backfilled with N$_2$ 3 times. In a separate flask, a mixture of toluene, H$_2$O (2:1) was bubbled with N$_2$ for 10 minutes. This degassed solvent was then added to the reaction flask under an N$_2$ atmosphere via syringe and placed into a preheated 100° C. oil bath and allowed to stir overnight. When completed, the reaction was removed from the oil bath and allowed to cool to room temperature before being washed with 2M HCl and extracted using EtOAc. The organic layers were collected, dried with Na$_2$SO$_4$, filtered, and the solvent was removed under reduced pressure. The crude solid was dissolved in a minimum amount of CH$_2$Cl$_2$ and precipitated into MeOH. H was isolated by filtration.

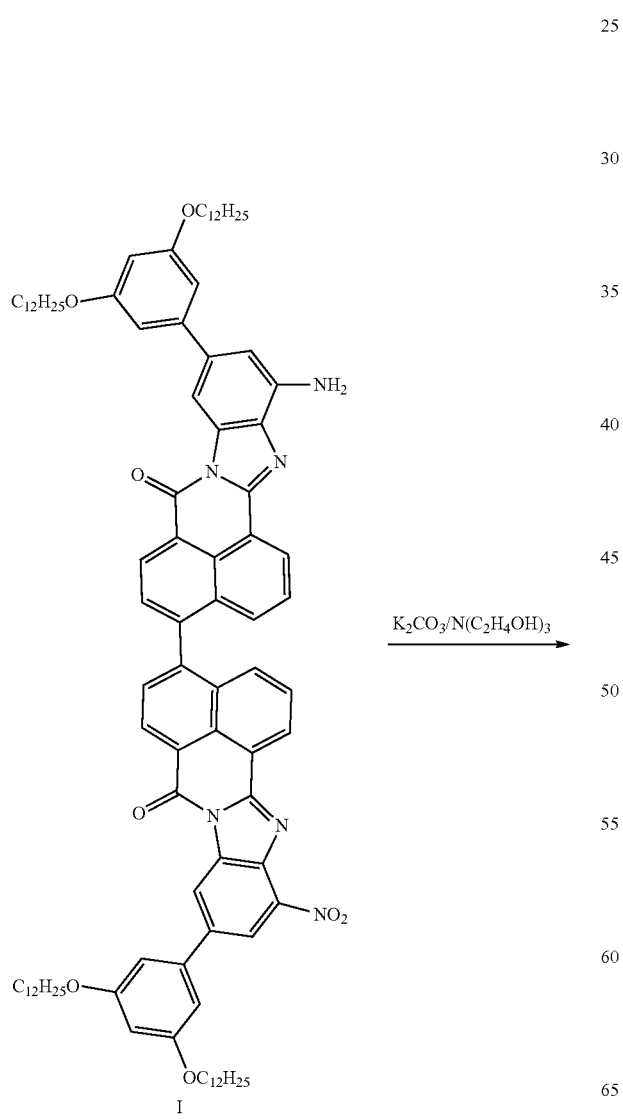

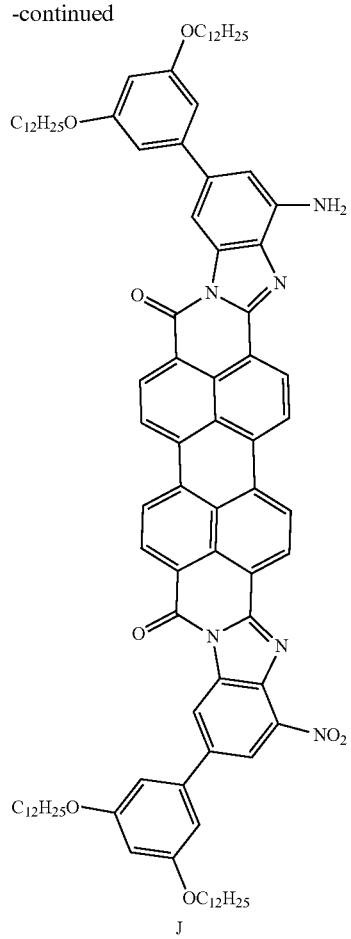

I (1 eq.) was dispersed in triethanolamine (0.02 M) and K$_2$CO$_3$ (25 eq.) was added. The mixture was stirred at 130° C. for 24 hours under argon atmosphere. Upon cooling to room temperature, the reaction mixture was diluted with dichloromethane and washed with water. The organic layer was dried over anhydrous sodium sulfate and purified by precipitation into methanol to yield J as dark purple solid.

Example 2

This Example describes synthesis of the disclosed organic compound according following structural scheme:

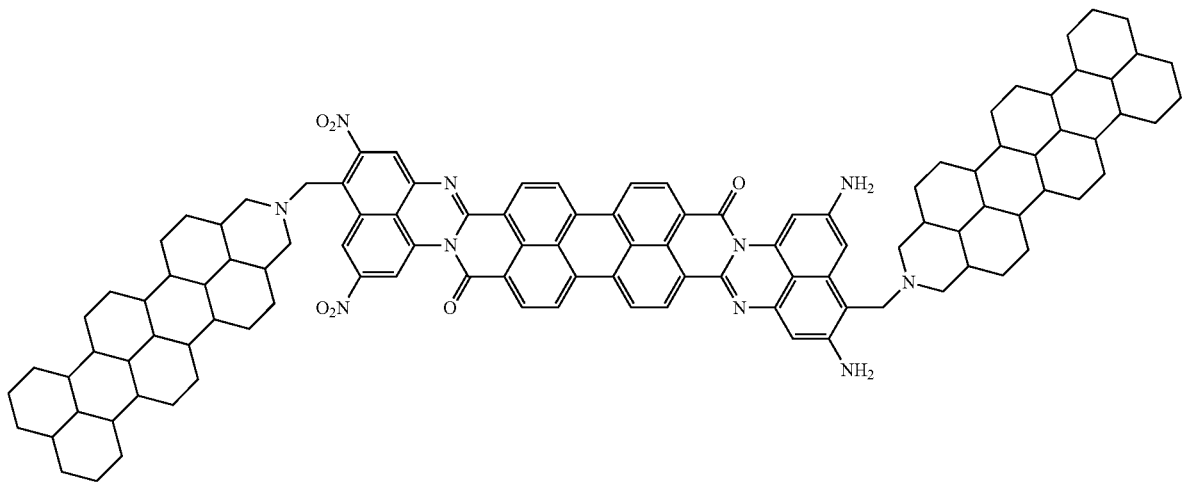 [SMILES: Nc1cc2c(CN3CC4CCC5C6CCC7C8CCCC9CCCC(C%10CCC(C%11CCC(C3)C4C5%11)C6C7%10)C98)c(N)cc3nc4c5ccc6c7ccc8c(=O)n9c%10cc([N+](=O)[O-])cc%11c(CN%12CC%13CCC%14C%15CCC%16C%17CCCC%18CCCC(C%19CCC(C%20CCC(C%12)C%13C%14%20)C%15C%16%19)C%18%17)c([N+](=O)[O-])cc(nc9c9ccc(c%12ccc(c(=O)n4c(c1)c32)c5c6%12)c7c89)c%11%10]

Procedure:

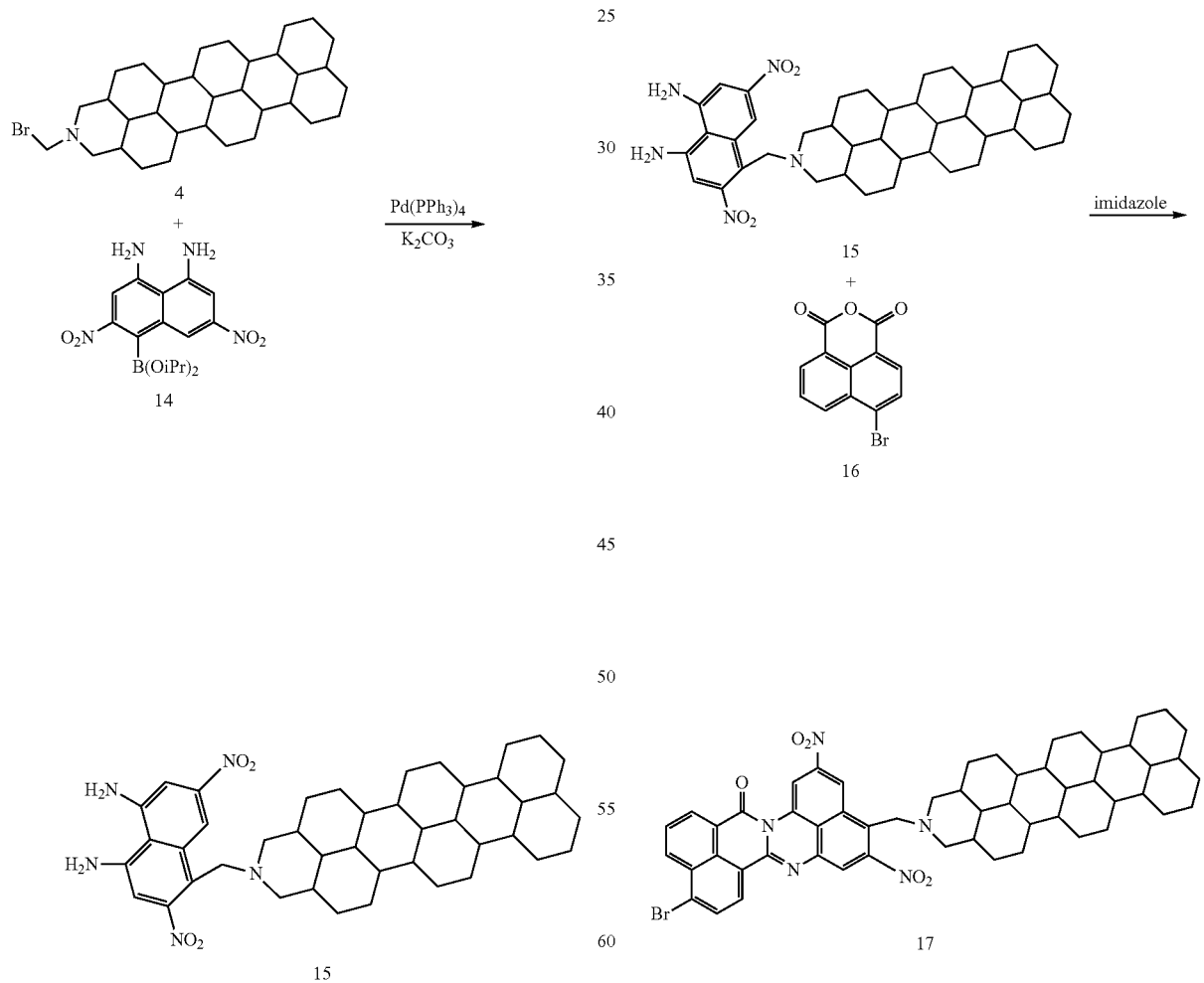

Bromo-amine 4 (1 eq.), Naphthalene 14 (1 eq.), Pd(PPh$_3$)$_4$ (10 mol %), K$_2$CO$_3$ (1.5 eq.) were stirred in toluene at 70° C. for 18 h. The mixture was filtered through Diatomaceous earth and the filtrate was washed with NaHCO$_3$ and brine. The organics were dried over MgSO$_4$, and the solvents were removed under reduced pressure to give 15.

Naphthalene anhydride 16 (1 eq.) and naphthalene 15 (1 eq.) were stirred in imidazole at 130° C. overnight. The mixture was dissolved in THF and washed with water 3 times. The organics were combined and dried over MgSO$_4$. The solvent was removed under reduced pressure to give 17.

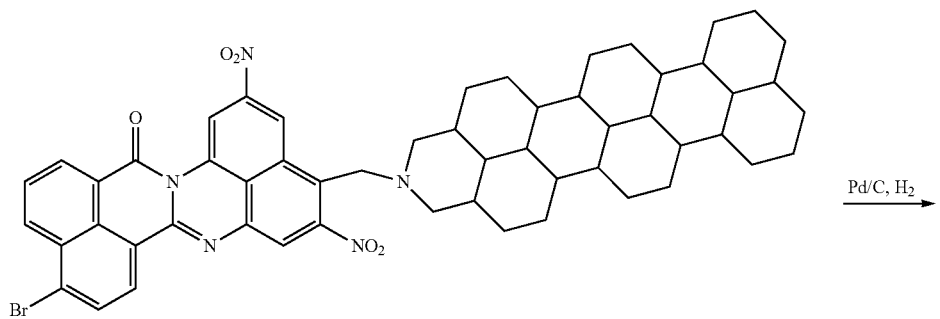

17

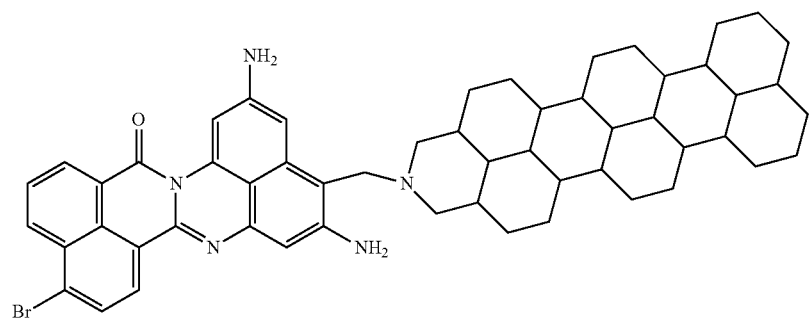

18

Amidine 17 (1 eq.) and Pd/C (20% wt/wt) were stirred in THF in a three-neck flask with a H₂ balloon attached for 18 h. The mixture was filtered through Diatomaceous earth and the solvents were removed under reduced pressure to give 18.

Amidine 17 (1 eq.) was dissolved in THF and stirred at −80° C. N-butyllithium (1.2 eq., 2.5 M in hexanes) was added dropwise. After 1 h, triisopropylborane was added dropwise and allow to warm to room temperature overnight. The mixture was washed with NaHCO₃ and brine and dried over MgSO₄. The solvent was removed under reduced pressure to give 19.

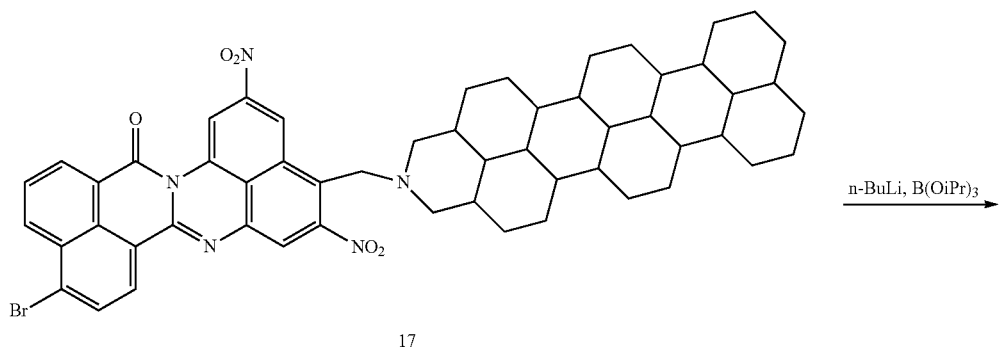

17

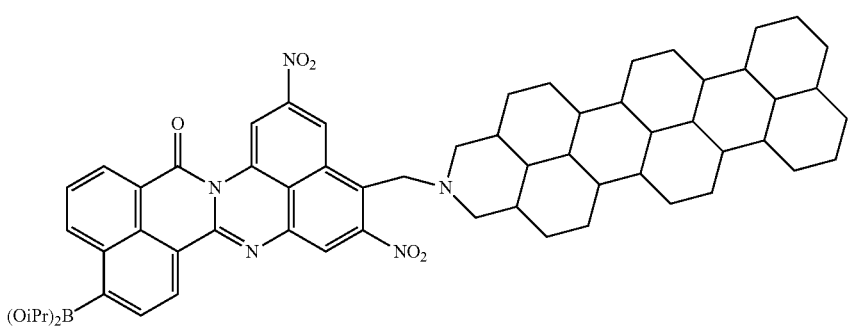

19

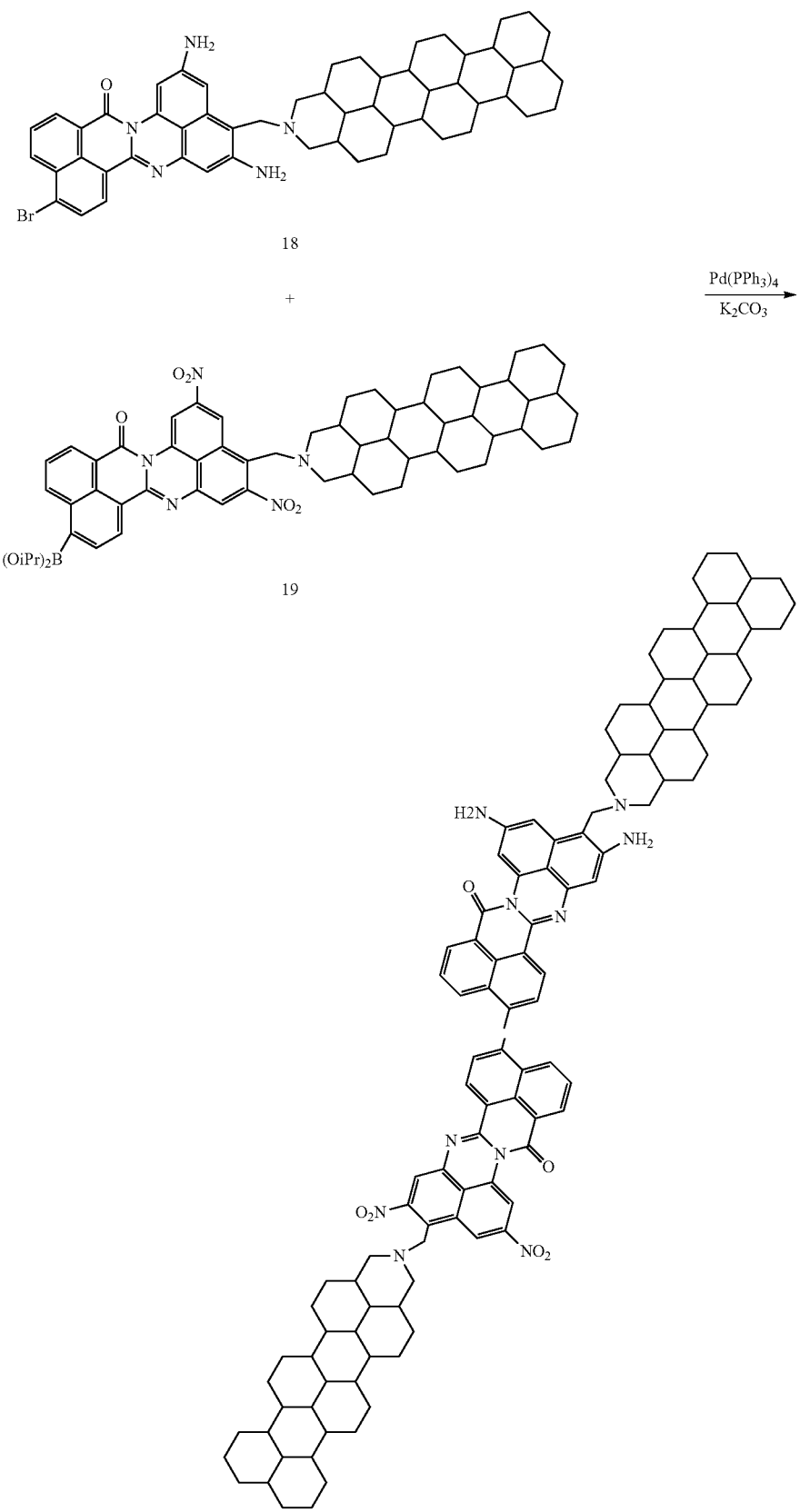

Bromo-amidine 18 (1 eq.), Amidine boronic ester 19 (1 eq.), Pd(PPh$_3$)$_4$ (10 mol %), K$_2$CO$_3$ (1.5 eq.) were stirred in toluene at 70° C. for 18 h. The mixture was filtered through Diatomaceous earth and the filtrate was washed with NaHCO$_3$ and brine. The organics were dried over MgSO$_4$, and the solvents were removed under reduced pressure to give 20.
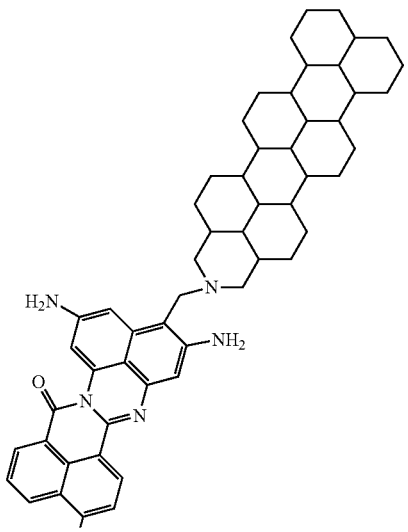
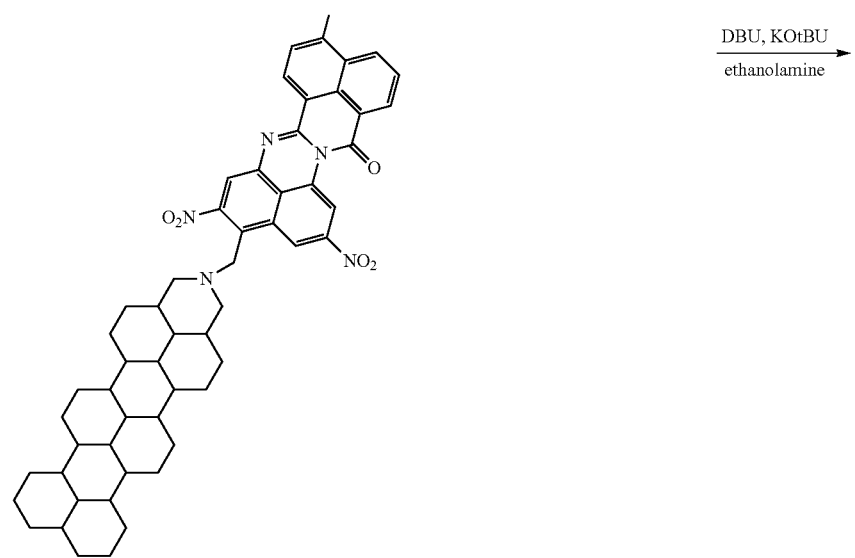
20

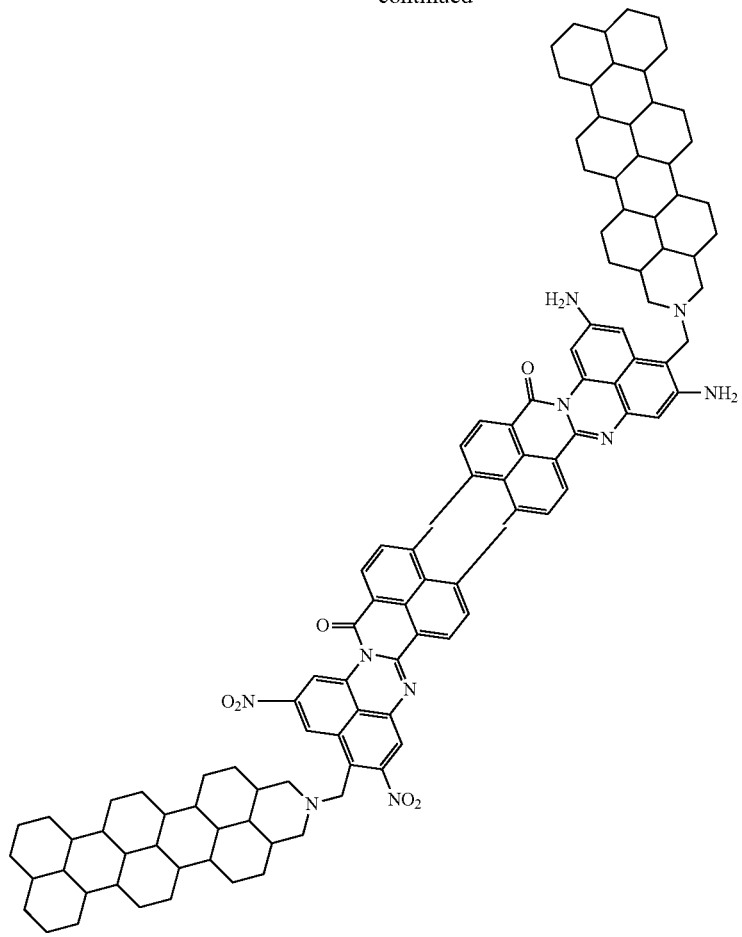

21

A mixture of potassium tert-butoxide (1 eq), diazabicyclo [5.4.0]undec-7-ene (DBU) (1.2 eq.), ethanolamine (2.8 eq.) and 20 (1 eq.) was heated to 140° C. for 11 hours. Afterwards, the same amount of potassium tert-butoxide, DBU and ethanolamine were added and the mixture was kept at 140° C. for 18 hours. The reaction mixture was cooled to room temperature, poured into 1M HCl, filtered, washed until neutral pH and then dried to give the final product 21.

Aspects of the present disclosure provide compounds characterized by highly nonlinear electric polarizability. Such compounds are useful as high dielectric constant metadielectrics for metacapacitors with extremely high capacitance and extremely high energy storage capacity. While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. As used herein, in a listing of elements in the alternative, the word "or" is used in the logical inclusive sense, e.g., "X or Y" covers X alone, Y alone, or both X and Y together, except where expressly stated otherwise. Two or more elements listed as alternatives may be combined together. The appended claims are not to be interpreted as including means-plus-function limitations, unless such a limitation is explicitly recited in a given claim using the phrase "means for."

What is claimed is:

1. An electro-polarizable compound having the following formula (I):

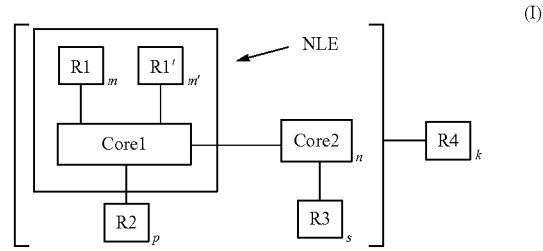

where Core1 is an aromatic polycyclic conjugated molecule having two-dimensional flat form supramolecular structures, R1 are electron donor groups selected from: $-O^-$, $-NH_2$, $-NHR$, $-NR_2$, $-NRR'$, $-OH$, $-OR$, —NHCOR, —OCOR, alkyls, —C$_6$H$_5$, vinyls, wherein R and R' are radicals independently selected from the list comprising alkyl, allyl, benzyl groups, phenyl, substituted phenyl, and aryl groups, connected to the aromatic polycyclic conjugated molecule (Core1) and R1' are electron acceptor groups selected from: —NO$_2$, —NH$_3^+$ and —NR$_3^+$, counterion Cl$^-$ or Br$^-$, —CHO, —CRO, —SO$_3$H, —SO$_3$R, —SO$_2$NH$_2$, —SO$_2$NHR, —SO$_2$NR$_2$, —COOH, —COOR, —CONH$_2$, —CONHR, —CONR$_2$, —CF$_3$, —CCl$_3$, —CN, C(CN)$_2$ wherein R is radical selected from the list comprising alkyl, allyl, benzyl groups, phenyl, substituted phenyl, and aryl groups, SO$_2$CN, COCF$_3$, connected to the aromatic polycyclic conjugated molecule (Core1), m is number of acceptor groups R1, m' is a number of donor groups R', m and m' are equal to 0, 1, 2, 3, 4, 5 or 6, wherein m and m' are not both equal to 0, R2 is a substituent comprising one or more ionic groups from a class of ionic compounds that are used in ionic liquids connected to the aromatic polycyclic conjugated molecule (Core1) directly or via a connecting group, p is a number of ionic groups R2 which is equal to 0, 1, 2, 3 or 4;

wherein the aromatic polycyclic conjugate molecule having two-dimensional flat form supramolecular structures (Core 1) comprises rylene fragment structures selected from:

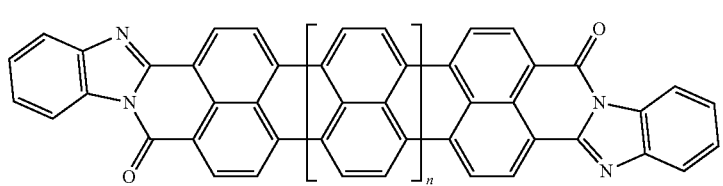

1

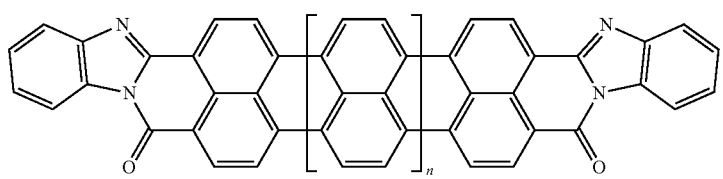

2

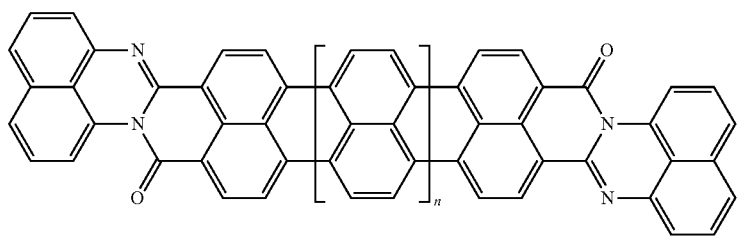

3

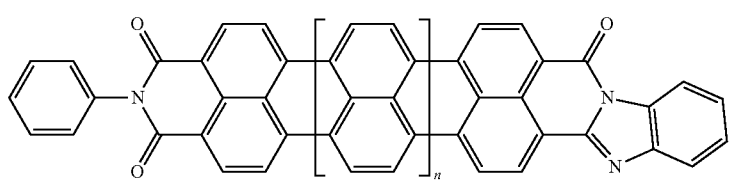

4

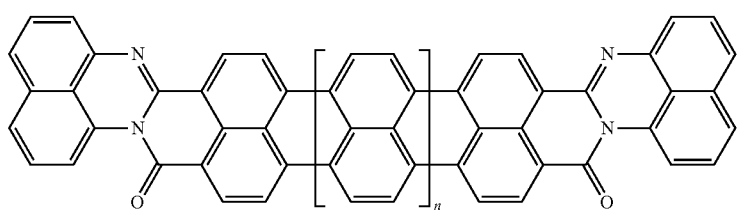

5

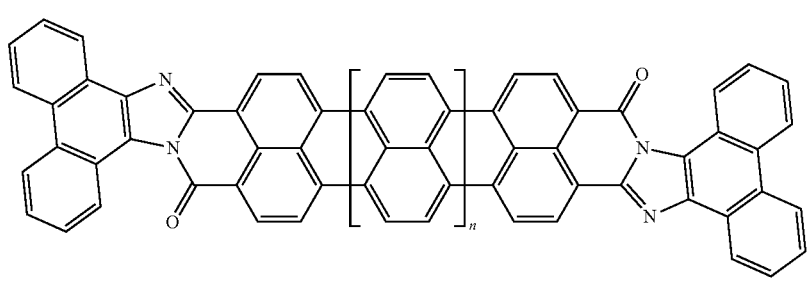

6

-continued
7
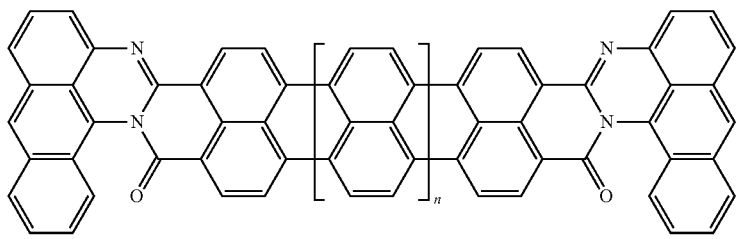
8
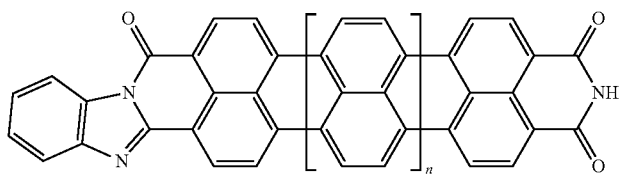
9
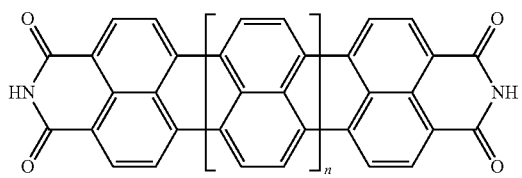
10
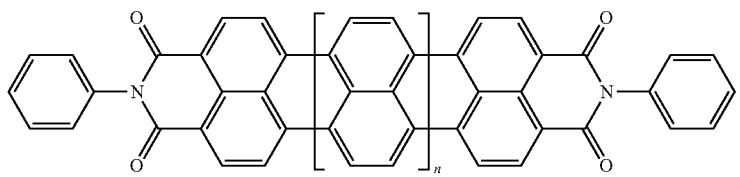
11
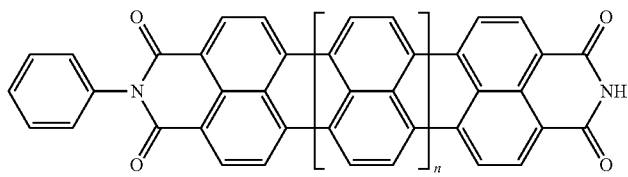
12
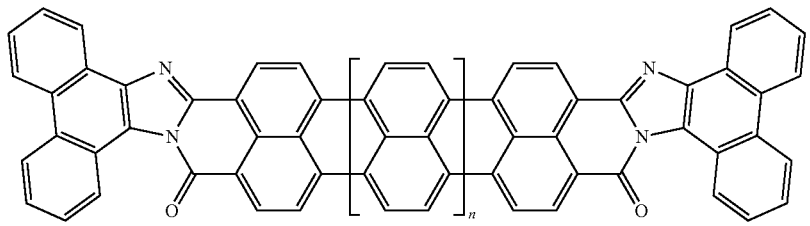
13
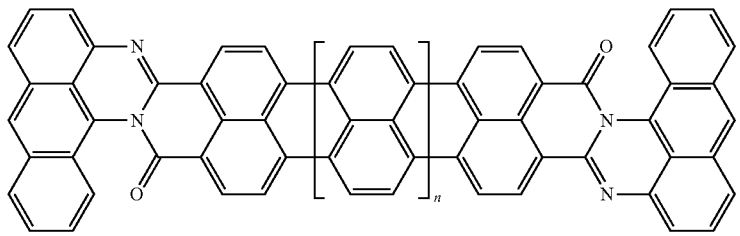

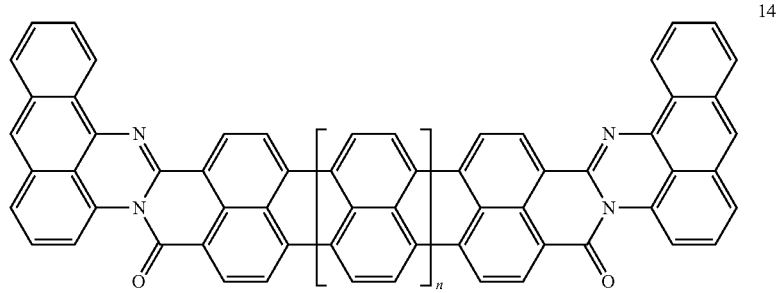

14

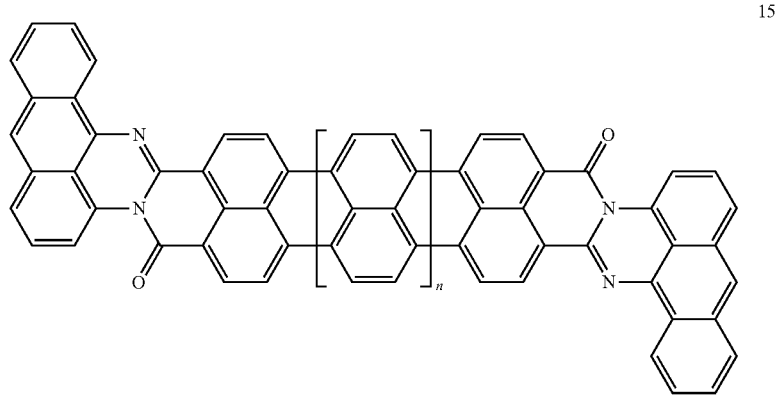

15

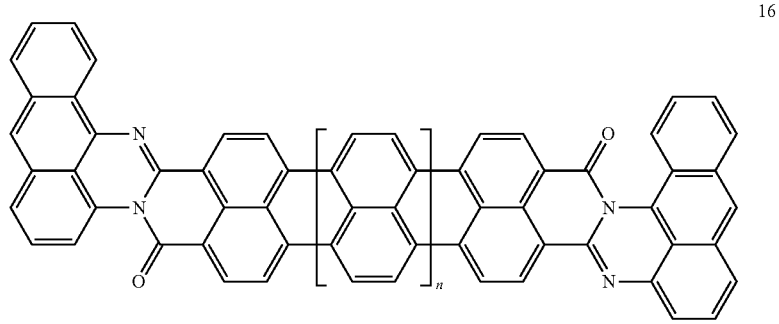

16

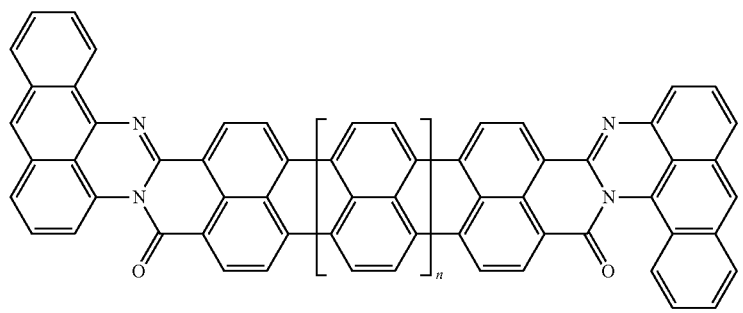

17 wherein n is an integer from 0-3;

wherein the fragment marked NLE containing the Core1 with at least one group R1 and/or R1' has a nonlinear effect of polarization, wherein Core2 is an electro-conductive oligomer, n is a number of the electro-conductive oligomers which is equal to an integer from 0-4, R3 is a substituent comprising one or more ionic groups from a class of ionic compounds that are used in ionic liquids connected to the electro-conductive oligomer (Core2) directly or via a connecting group, s is a number of the ionic groups R3 which is equal to 0, 1, 2, 3 or 4;

wherein the electro conductive oligomers are selected from phenylene, thiophene, or substituted and/or unsubstituted polyacene quinine radical oligomer of lengths ranging from 2 to 12 or combination of two or more of these, wherein the substitutions of ring hydrogens by O, S or NR5, and R5 is selected from the group consisting of unsubstituted or substituted $C_1$-$C_{18}$ alkyl, unsubstituted or substituted $C_2$-$C_{18}$ alkenyl, unsubstituted or substituted $C_2$-$C_{18}$ alkynyl, and unsubstituted or substituted $C_4$-$C_{18}$ aryl;

wherein R4 is a resistive substituent selected from the group of alkyl, aryl, substituted alkyl, substituted aryl, halo-alkyl, branched and complex alkyl, branched and complex halo-alkyl, benzyl groups, benzyl alkoxy groups, benzyl halo-alkoxy groups, alkoxy groups, benzyl alkyl groups, benzyl halo-alkyl groups, halo-alkoxy groups, benzyl aryl groups, and benzyl halo-aryl groups, and any combination there of, connected to the aromatic polycyclic conjugated molecule (Core1) and/or to the electro-conductive oligomer (Core2) directly or via a connecting group, k is a number of substituents R4 which is equal to 1, 2, 3, 4, 5, 6, 7 or 8.

2. The electro-polarizable compound according to claim 1, wherein the connecting group is selected from the list comprising $CH_2$, $CF_2$, $SiR_2O$, $CH_2CH_2O$, wherein R is selected from the list comprising H, alkyl, and fluorine; structures 18-35

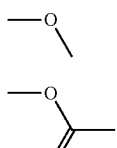

18

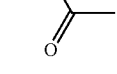

19

20

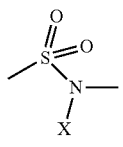

21

22

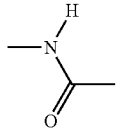

23

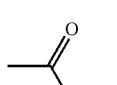

24

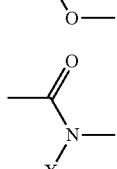

25

26

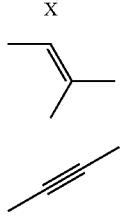

27

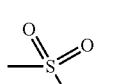

28

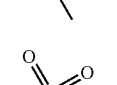

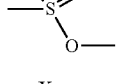

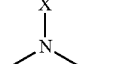

-continued

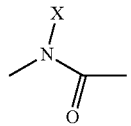

29

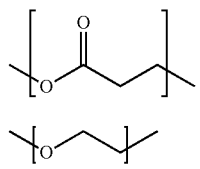

30

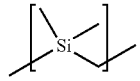

31

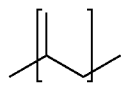

32

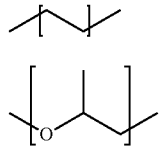

33

34

35

And where X is hydrogen (H) or an alkyl group.

3. The electro-polarizable compound according to claim 1, wherein the resistive substituent R4 is $C_XQ_{2X+1}$, where $X \geq 1$ and Q is selected from the list comprising of hydrogen (H), fluorine (F), and chlorine (Cl).

4. The electro-polarizable compound of claim 1, wherein the aromatic polycyclic conjugated molecule (Core1) and the groups R1 and R1' form a non-centrosymmetric molecular structure.

5. The electro-polarizable compound of claim 1, wherein the aromatic polycyclic conjugated molecule (Core1), the groups R1 and R1' and the resistive substituents (R4) form a non-centrosymmetric molecular structure.

6. The electro-polarizable compound of claim 1 having the following formula (II):

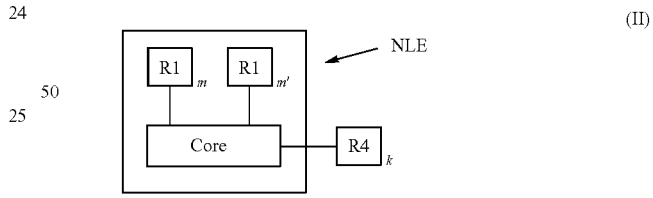

(II)

wherein the Core1 is the aromatic polycyclic conjugated molecule, resistive substituents R4 are a non-conjugated part of compound II, and wherein k is a number of substituents R4 which is equal to 1, 2, 3, 4, 5, 6, 7 or 8 and parameters n=p=s=0.

7. The electro-polarizable compound of claim 6, wherein a length of the non-conjugated part is selected such that resistivity of the electro-polarizable compound is greater than or equal to $10^{15}$ ohm·cm.

8. The electro-polarizable compound of claim 6, wherein the resistive substituent R4 is comprised of a polycyclic alkyl group and a polycyclic halo-alkyl group, wherein in the polycyclic halo-alkyl group is connected to the apex of Core1 on which the electrophilic group (acceptor) R1 is connected, or the apex of Core1 on which the nucleophilic group (donor) R1' is connected.

9. The electro-polarizable compound of claim 6 wherein the resistive substituent R4 is selected from the group of alkyl, aryl, substituted alkyl, substituted aryl, halo-alkyl, branched and complex alkyl, branched and complex halo-alkyl, benzyl groups, benzyl alkoxy groups, benzyl halo-alkoxy groups, alkoxy groups, benzyl alkyl groups, benzyl halo-alkyl groups, halo-alkoxy groups, benzyl aryl groups, and benzyl halo-aryl groups, and any combination thereof.

10. A metadielectric layer, comprising a layer of material containing one or more electro-polarizable compounds of claim 1.

11. A metadielectric layer comprised of the electro-polarizable compound according to claim 1, wherein the nonlinearly polarizable fragments comprising an aromatic polycyclic conjugated molecule with at least one R4 group, and wherein the at least R4 groups form a resistive envelope electrically insulating the supramolecular structures from each other.

12. A metadielectric layer comprised of one or more supramolecular structures, wherein the supramolecular structures are formed by the electro-polarizable compounds according to claim 1, comprising rylene fragments of different length.

13. The metadielectric layer according to claim 10, wherein the metadielectric layer's relative permittivity is greater than or equal to 1000 and wherein the layer's resistivity is greater than or equal to $10^{15}$ ohm·cm.

14. A meta-capacitor comprising two metal electrodes positioned parallel to each other and which can be rolled or flat and planar with said metadielectric layer between said electrodes, wherein the metadielectric layer comprises one or more types of the electro-polarizable compounds according to claim 1 wherein the nonlinearly polarizable fragments comprising an aromatic polycyclic conjugated molecule with at least one group R1 or R1', the electro-conductive oligomers and the ionic groups which have electronic and/or ionic type of polarizability are placed into a resistive dielectric envelope formed by resistive substituents, R4, electrically insulating the supramolecules from each other.

* * * * *